United States Patent
Yamada

(10) Patent No.: US 10,444,154 B2
(45) Date of Patent: Oct. 15, 2019

(54) NITRIC OXIDE DETECTION METHOD

(71) Applicant: Seiko Epson Corporation, Tokyo (JP)

(72) Inventor: Kohei Yamada, Suwa (JP)

(73) Assignee: Seiko Epson Corporation (JP)

( * ) Notice: Subject to any disclaimer, the term of this patent is extended or adjusted under 35 U.S.C. 154(b) by 259 days.

(21) Appl. No.: 15/248,166

(22) Filed: Aug. 26, 2016

(65) Prior Publication Data

US 2017/0067831 A1 Mar. 9, 2017

(30) Foreign Application Priority Data

Sep. 7, 2015 (JP) ................................. 2015-175684

(51) Int. Cl.
*G01N 21/65* (2006.01)
*G01N 21/77* (2006.01)

(52) U.S. Cl.
CPC ........... *G01N 21/658* (2013.01); *G01N 21/77* (2013.01)

(58) Field of Classification Search
CPC ..................................................... G01N 21/65
USPC ........................ 422/82.05; 436/116, 164, 171
See application file for complete search history.

(56) References Cited

U.S. PATENT DOCUMENTS

| | | | | |
|---|---|---|---|---|
| 4,573,791 A | * | 3/1986 | Phillips ..................... | G03F 9/70 355/43 |
| 5,525,520 A | * | 6/1996 | Dinh ........................ | G01N 21/75 422/82.06 |
| 5,526,121 A | * | 6/1996 | Sandifer ..................... | G01J 3/02 250/351 |
| 5,828,450 A | * | 10/1998 | Dou ........................ | G01J 3/4412 356/301 |
| 6,159,681 A | * | 12/2000 | Zebala .................. | B01J 19/0046 430/56 |
| 6,174,677 B1 | * | 1/2001 | Vo-Dinh .............. | C12Q 1/6825 356/301 |

(Continued)

FOREIGN PATENT DOCUMENTS

JP H08-304284 A 11/1996
JP 2005-091353 A 4/2005

(Continued)

OTHER PUBLICATIONS

Shi, C. et al, Journal of Physical Chemistry 1990, 94, 4766-4769.*

(Continued)

*Primary Examiner* — Arlen Soderquist
(74) *Attorney, Agent, or Firm* — Harness, Dickey & Pierce, P.L.C.

(57) ABSTRACT

A substance detection method includes exposing a sensor chip for surface-enhanced Raman scattering having a metal microstructure and an organic molecular modification film which modifies the metal microstructure to a first gas, irradiating a first region of the sensor chip exposed to the first gas with first laser light, performing first measurement by acquiring the intensity of Raman scattered light from the first region, blocking the first laser light after the performing the first measurement, and adjusting an irradiation region where the sensor chip is irradiated with the first laser light from the first region to a second region which is different from the first region of the sensor chip after the blocking the first laser light.

6 Claims, 15 Drawing Sheets

(56) References Cited

U.S. PATENT DOCUMENTS

| | | | | |
|---|---|---|---|---|
| 6,416,959 B1* | 7/2002 | Giuliano | | C12Q 1/68 250/201.3 |
| 6,713,264 B2* | 3/2004 | Luttermann | | G01N 15/1468 356/337 |
| 6,795,177 B2* | 9/2004 | Doyle | | G01J 3/44 356/301 |
| 8,535,115 B2* | 9/2013 | David | | B24B 37/013 356/614 |
| 8,773,658 B2 | 7/2014 | Yamada et al. | | |
| 10,060,855 B2* | 8/2018 | Yamada | | C09K 9/02 |
| 2002/0137091 A1* | 9/2002 | Luttermann | | G01N 15/1468 435/7.1 |
| 2004/0096981 A1* | 5/2004 | Weimer | | G01N 21/658 436/171 |
| 2004/0147035 A1* | 7/2004 | Nagano | | C07D 311/90 436/118 |
| 2006/0074282 A1* | 4/2006 | Ward | | A61B 5/0071 600/310 |
| 2006/0142662 A1* | 6/2006 | Van Beek | | A61B 5/0059 600/476 |
| 2006/0258942 A1* | 11/2006 | Van Beek | | A61B 5/0059 600/477 |
| 2007/0172894 A1* | 7/2007 | Genick | | B01L 3/5085 435/7.2 |
| 2007/0247620 A1* | 10/2007 | Koo | | G01J 3/44 356/301 |
| 2008/0088952 A1* | 4/2008 | Unger | | G01N 21/6452 359/798 |
| 2009/0135417 A1* | 5/2009 | Carron | | G01J 3/02 356/301 |
| 2010/0081159 A1* | 4/2010 | Lebedeva | | C12Q 1/02 435/29 |
| 2010/0086439 A1* | 4/2010 | Yamanaka | | G01N 21/77 422/52 |
| 2010/0291599 A1* | 11/2010 | Tague, Jr. | | G01J 3/44 435/7.92 |
| 2011/0045523 A1* | 2/2011 | Strano | | G01N 21/6428 435/29 |
| 2011/0267613 A1* | 11/2011 | Amako | | G01N 21/554 356/301 |
| 2011/0311970 A1* | 12/2011 | Shachaf | | G01N 33/5008 435/6.11 |
| 2012/0162640 A1* | 6/2012 | Sakagami | | G01N 21/658 356/301 |
| 2012/0223130 A1* | 9/2012 | Knopp | | G01N 21/3586 235/375 |
| 2012/0236301 A1* | 9/2012 | Hashimoto | | G01N 21/658 356/301 |
| 2012/0257198 A1* | 10/2012 | Yamada | | G01N 21/658 356/301 |
| 2012/0262718 A1* | 10/2012 | Yamada | | G01N 29/022 356/436 |
| 2012/0274935 A1* | 11/2012 | Yamada | | G01N 21/05 356/301 |
| 2012/0327417 A1* | 12/2012 | Amako | | G01N 21/658 356/445 |
| 2013/0092823 A1* | 4/2013 | Amako | | G01N 21/554 250/216 |
| 2013/0278928 A1* | 10/2013 | Mourey | | G01N 21/274 356/301 |
| 2013/0302903 A1* | 11/2013 | Anslyn | | C07C 255/58 436/116 |
| 2014/0080122 A1* | 3/2014 | Strano | | G01N 21/6428 435/6.1 |
| 2014/0118731 A1* | 5/2014 | Ayers | | G01J 3/0237 356/301 |
| 2014/0120574 A1* | 5/2014 | Anslyn | | A61K 31/455 435/34 |
| 2014/0166863 A1* | 6/2014 | Yamada | | G01N 21/65 250/216 |
| 2014/0310839 A1* | 10/2014 | Wickramasinghe | | G01Q 30/02 850/40 |
| 2014/0333723 A1* | 11/2014 | Dowaki | | G01N 21/65 348/46 |
| 2015/0064778 A1* | 3/2015 | Yamada | | G01N 33/0047 435/288.7 |
| 2015/0098085 A1* | 4/2015 | Mano | | G01N 21/658 356/445 |
| 2015/0103347 A1* | 4/2015 | Sugimoto | | G01N 21/658 356/364 |
| 2015/0109619 A1* | 4/2015 | Sugimoto | | G01N 21/658 356/445 |
| 2015/0131092 A1* | 5/2015 | Sakagami | | G01N 21/658 356/301 |
| 2015/0138543 A1* | 5/2015 | Sugimoto | | G01N 21/65 356/301 |
| 2015/0139856 A1* | 5/2015 | Yamada | | G01N 21/658 422/69 |
| 2015/0211930 A1* | 7/2015 | Yamada | | G01J 3/44 356/301 |
| 2015/0233822 A1* | 8/2015 | Sugimoto | | G01N 21/553 356/369 |
| 2015/0279616 A1* | 10/2015 | Jiruse | | G01J 3/44 850/9 |
| 2016/0011117 A1 | 1/2016 | Strola et al. | | |
| 2016/0091366 A1* | 3/2016 | Yang | | G01J 3/0237 356/301 |
| 2017/0079556 A1* | 3/2017 | Hano | | A61B 5/082 |
| 2017/0160203 A1* | 6/2017 | Yamada | | C09K 9/02 |

FOREIGN PATENT DOCUMENTS

| | | |
|---|---|---|
| JP | 2007-117782 A | 5/2007 |
| JP | 2012-198059 A | 10/2012 |
| JP | 2012-230042 A | 11/2012 |
| JP | 2014-190915 A | 10/2014 |
| WO | WO-2014-118263 A1 | 8/2014 |

OTHER PUBLICATIONS

Quaroni, L. et al, Biochimica et Biophysica Acta 1996, 1296, 5-8.*
Dick, L. A. et al, Journal of Physical Chemistry B 2000, 104, 11752-11762.*
De Jesus, M. A. et al, Journal or Raman Spectroscopy 2004, 35, 895-904.*
Shachaf, C. M. et al, PLoS ONE 2009,4, e5206, 12 pages.*
Kong, C.-R. et al, AIP Advances 2011,1, 032175, 13 pages.*
Maiti, K. K. et al, Nano Today 2012, 7, 85-93.*
Palonpon, A. F. et al, Nature Protocols 2013, 8, 677-692.*
Lim, J. K. et al, Chemical Physics 2006, 330, 245-252.*
Ye, X. et al, Journal of Neuroscience Methods 2008, 168, 373-382.*
Vangala, K. et al, Analytical Chemistry 2010, 82, 10164-10171.*
Yu, M.-R. et al, Sensors and Actuators B 2012, 161, 938-947.*
Alvarez-Puebla, R. A. et al, Angew.andte Chemie International Edition 2012, 51, 11214-11223.*
Qu, L.-L. et al, Analytica Chimica Acta 2013, 792, 86-92.*
Rivera_Gil, P. et al, Angew.andte Chemie International Edition 2013, 52, 13694-13698.*
Drago, R. S. et al, Journal of the American Chemical Society1961, 83, 8, 1819-1822.*
Laserna, J. J. et al, Analytica Chimica Acta 1987, 200, 469-480.*
Itoh, T. et al, Journal of Organic Chemistry 1997, 62, 3582-3585.*
Barker, S. L. R. et al, Analytical Chemistry 1998, 70, 4902-4906.*
Barker, S. L. R., Dissertation 1999, 133 pages.*
Kojima, H. et al, Analytical Chemistry 2001, 73, 1967-1973.*
Emory, S. R. et al, SPIE 2001, 4258, 63-72.*
McNay, Graeme and David Eustace et al., "Surface-Enhanced Raman Scattering (SERS) and Surface-Enhanced Resonance Raman Scattering (SERS): A Review of Applications", Applied Spectroscopy, vol. 65, No. 8, pp. 825-837 (May 2011).
Bryan, Nathan S. and Matthew B. Grisham, "Methods to detect nitric oxide and its metabolites in biological samples", Free Radical Biology & Medicine, vol. 43, pp. 645-657 (Apr. 2007).

(56) References Cited

OTHER PUBLICATIONS

Nagano, Tetsuo et al.; "Reactions of Nitric Oxide with Amines in the Presence of Dioxygen", Tetrahedron Letters, vol. 36, No. 45, pp. 8239-8242 (1995).

* cited by examiner

NITRIC OXIDE DETECTION METHOD

BACKGROUND

1. Technical Field

The present invention relates to a substance detection method and a substance detection device.

2. Related Art

Recently, as a highly sensitive spectroscopic technique for detecting a sample molecule at a low concentration, an affinity sensor utilizing localized surface plasmon resonance (LSPR) or surface-enhanced Raman scattering (SERS) for qualitative and quantitative detection directly from vibrational spectroscopy has attracted attention. SERS is spectroscopy in which an enhanced electric field is formed on a metal surface with a nanometer-scale convex-concave structure, and Raman scattered light is enhanced by $10^2$ times to $10^4$ times, thereby enabling highly sensitive detection. A target molecule (target substance) is irradiated with linearly polarized excitation light with a single wavelength such as a laser, and scattered light (Raman scattered light) with a wavelength which is shifted from the wavelength of the excitation light by the molecular vibration energy of the target molecule is spectroscopically detected, whereby a fingerprint spectrum is obtained. Based on the shape of this fingerprint spectrum, the target substance can be identified.

It has been confirmed that there is a correlation between tracheal inflammation due to asthma and the concentration of NO (nitrogen monoxide) contained in the breath, and the concentration of NO in the breath has been recognized as an index of asthma. As a sensor chip for detecting such NO, a sensor chip focusing on surface plasmon resonance (SPR) which is a light sensing technique has been proposed. For example, APPLIED SPECTROSCOPY, Volume 65, Number 8, 825-837, 2011 (NPL 1) describes that a biological enzyme called "cytochrome P450" is disposed on an LSPR substrate (sensor chip) having an Ag microstructure, and NO is allowed to react with the cytochrome P450 enzyme, and the SERS signal of the reactant is obtained.

However, when a sensor chip having an organically modified film for trapping NO (target substance) as described above is irradiated with laser light, the organically modified film may sometimes be deteriorated by the laser light. Due to this, NO cannot be detected with high sensitivity in some cases.

SUMMARY

An advantage of some aspects of the invention is to provide a substance detection method capable of detecting a target substance with high sensitivity. Further, another advantage of some aspects of the invention is to provide a substance detection device capable of detecting a target substance with high sensitivity.

A substance detection method according to an aspect of the invention includes exposing a sensor chip for surface-enhanced Raman scattering having a metal microstructure and an organic molecular modification film which modifies the metal microstructure to a first gas, irradiating a first region of the sensor chip exposed to the first gas with first laser light, performing first measurement by acquiring the intensity of Raman scattered light from the first region, blocking the first laser light after the performing the first measurement, and adjusting an irradiation region where the sensor chip is irradiated with the first laser light from the first region to a second region which is different from the first region of the sensor chip after the blocking the first laser light.

According to such a substance detection method, in the subsequent measurement, the second region of the sensor chip which is not yet irradiated with laser light is irradiated with laser light and Raman scattered light can be detected. Therefore, according to such a substance detection method, the deterioration of the organic molecular modification film of the sensor chip by the laser light can be suppressed. As a result, according to such a substance detection method, a target substance can be detected with high sensitivity.

In the substance detection method according to the aspect of the invention, in the adjusting the first laser light irradiation region to the second region, the sensor chip may be moved.

According to such a substance detection method, the irradiation region can be easily changed as compared with the case where a laser light irradiation region is changed by moving a light source or by changing the placement of a lens or the like.

In the substance detection method according to the aspect of the invention, in the performing the first measurement, the intensity of Raman scattered light may be acquired a plurality of times at predetermined intervals based on the timing of irradiation of the first region.

According to such a substance detection method, it is not necessary to wait until the intensity of Raman scattered light is brought into a saturated state, and thus, a time until the concentration of a target substance is calculated can be reduced.

In the substance detection method according to the aspect of the invention, the first gas may contain breath and air, and the method may include exposing the sensor chip to the air, irradiating a third region which is different from the first region and the second region of the sensor chip exposed to the air with the first laser light, acquiring the intensity of Raman scattered light from the third region, and calculating the concentration of a target substance in the breath based on the measurement result of the first measurement and the acquired intensity of Raman scattered light from the third region.

According to such a substance detection method, the concentration of NO (nitrogen monoxide) in the breath can be accurately calculated.

In the substance detection method according to the aspect of the invention, the method may include irradiating the first region with second laser light with a lower intensity than the first laser light through a lens before the irradiating the first laser light, acquiring the intensity of scattered light from the first region by the second laser light detected in a state where the lens is moved, and determining the position of the lens based on the acquired intensity of the scattered light from the first region, and in the irradiating the first laser light, the first region may be irradiated through the lens.

According to such a substance detection method, defocus caused by, for example, moving the sensor chip can be corrected while reducing the deterioration of the sensor chip by the irradiation with the laser light.

In the substance detection method according to the aspect of the invention, the organic molecular modification film may contain a modifying molecule derived from a compound having an amine-based or sulfur-based functional group, and the first gas may contain nitrogen monoxide.

According to such a substance detection method, NO can be detected with high sensitivity.

A substance detection device according to an aspect of the invention includes a sensor chip for surface-enhanced Raman scattering having a metal microstructure and an organic molecular modification film which modifies the metal microstructure, alight source which irradiates the sensor chip with laser light, a light detector which detects Raman scattered light from the sensor chip, a light-blocking filter capable of blocking the laser light, a light-blocking filter moving section which moves the light-blocking filter, and an irradiation region changing section which changes the laser light irradiation region in the sensor chip.

According to such a substance detection device, in the subsequent measurement, the second region of the sensor chip which is not yet irradiated with laser light is irradiated with laser light and Raman scattered light can be detected. Therefore, according to such a substance detection device, the deterioration of the organic molecular modification film of the sensor chip by the laser light can be suppressed. As a result, according to such a substance detection device, a target substance can be detected with high sensitivity.

In the substance detection device according to the aspect of the invention, the irradiation region changing section may change the laser light irradiation region by moving the sensor chip.

According to such a substance detection device, the irradiation region can be easily changed as compared with the case where a laser light irradiation region is changed by moving alight source or changing the placement of a lens or the like.

In the substance detection device according to the aspect of the invention, the device may include a first light intensity acquisition section which performs first measurement processing by acquiring the intensity of Raman scattered light from a first region of the sensor chip exposed to a first gas detected by the light detector, and an irradiation region changing processing section which performs processing of blocking the laser light by controlling the light-blocking filter moving section after the first measurement processing and adjusting the laser light irradiation region from the first region to a second region which is different from the first region of the sensor chip by controlling the irradiation region changing section.

According to such a substance detection device, by the irradiation region changing processing section, after the measurement (first measurement) regarding the intensity of Raman scattered light detected by the light detector is completed, the laser light irradiation region in the sensor chip can be changed in a state where the laser light is blocked.

In the substance detection device according to the aspect of the invention, the first light intensity acquisition section may acquire the intensity of Raman scattered light a plurality of times at predetermined intervals based on the timing of irradiation of the first region in the first measurement processing.

According to such a substance detection device, it is not necessary to wait until the intensity of Raman scattered light is brought into a saturated state, and thus, a time until the concentration of a target substance is calculated can be reduced.

In the substance detection device according to the aspect of the invention, the first gas may contain breath and air, and the device may include a second light intensity acquisition section which acquires the intensity of Raman scattered light from a third region which is different from the first region and the second region of the sensor chip exposed to the air detected by the light detector, and a breath concentration calculation section which calculates the concentration of a target substance in the breath based on the measurement result of the first measurement processing and the intensity of Raman scattered light acquired by the second light intensity acquisition section.

According to such a substance detection device, the concentration of NO in the breath can be accurately calculated.

In the substance detection device according to the aspect of the invention, the device may include a dimmer filter capable of decreasing the intensity of the laser light, a dimmer filter moving section which moves the dimmer filter, a lens which guides the laser light to the sensor chip, a lens moving section which moves the lens, a third light intensity acquisition section which acquires the intensity of scattered light from the first region by the laser light transmitted through the dimmer filter detected by the light detector in a state where the lens is moved by the lens moving section, and a lens position determination section which determines the position of the lens based on the intensity of the scattered light acquired by the third light intensity acquisition section.

According to such a substance detection device, defocus caused by, for example, moving the sensor chip can be corrected while reducing the deterioration of the sensor chip by the irradiation with the laser light.

In the substance detection device according to the aspect of the invention, the organic molecular modification film may contain a modifying molecule derived from a compound having an amine-based or sulfur-based functional group, and the first gas may contain nitrogen monoxide.

According to such a substance detection device, NO can be detected with high sensitivity.

BRIEF DESCRIPTION OF THE DRAWINGS

The invention will be described with reference to the drawings, wherein like numbers reference like elements.

DESCRIPTION OF EXEMPLARY EMBODIMENTS

Hereinafter, preferred embodiments of the invention will be described in detail with reference to the drawings. The embodiments described below do not unduly limit the contents of the invention described in the appended claims. Also, all of the configurations described below are not necessarily essential components of the invention.

1. First Embodiment

1.1. Substance Detection Device

Figure 1:
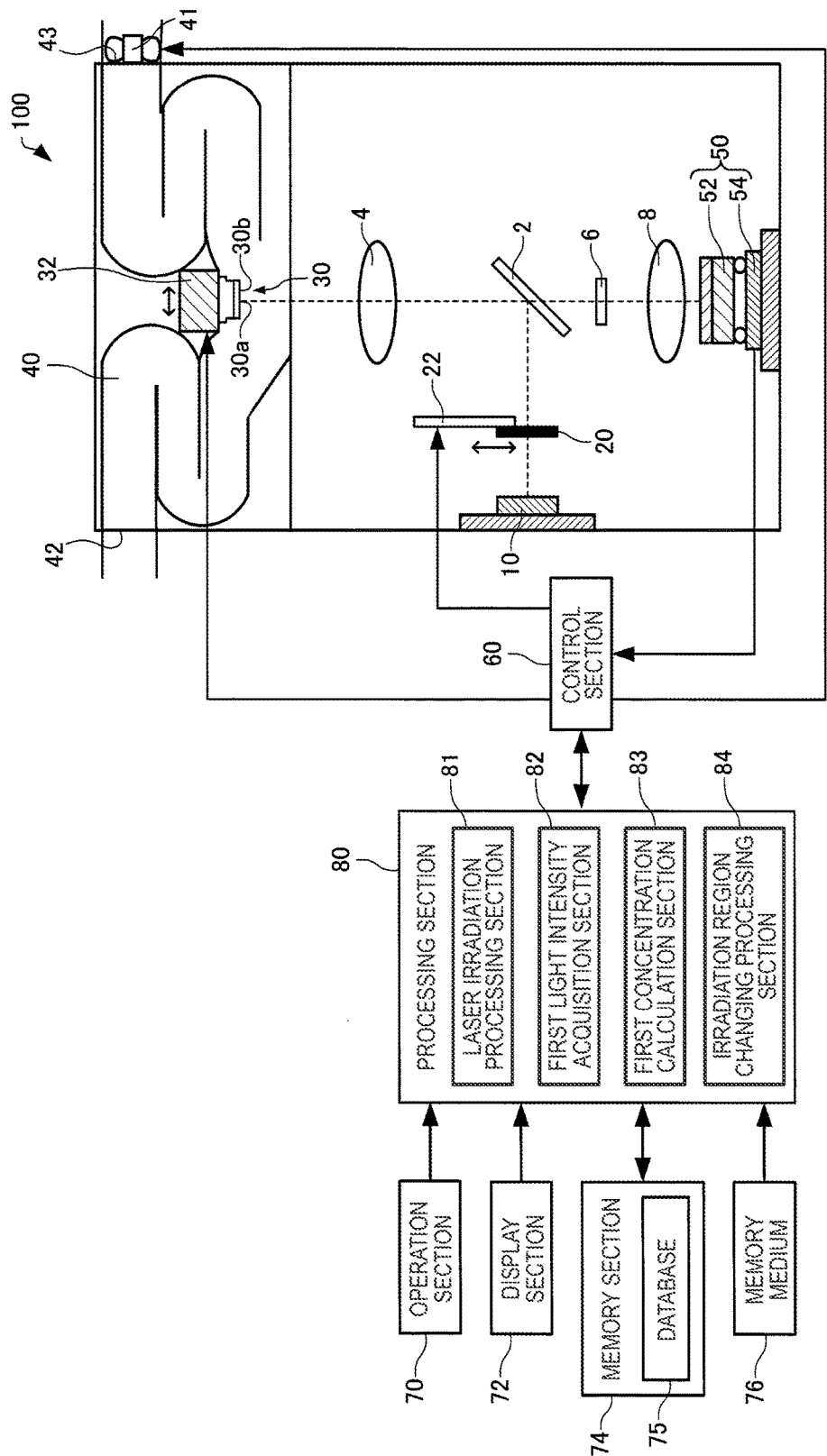
FIG. 1 is a view for explaining a substance detection device according to a first embodiment.

First, a substance detection device according to a first embodiment will be described with reference to the drawings. FIG. 1 is a view for explaining a substance detection device 100 according to the first embodiment.

As shown in FIG. 1, the substance detection device 100 includes a light source 10, a light-blocking filter 20, a light-blocking filter moving section 22, a sensor chip 30, an irradiation region changing section 32, a flow path 40, a light detector 50, a control section 60, an operation section 70, a display section 72, a memory section 74, a memory medium 76, and a processing section 80.

The light source 10 irradiates the sensor chip 30 with laser light. In an example shown in the drawing, a laser is incident on the sensor chip 30 through a half mirror 2 and a lens 4. The light source 10 is, for example, a semiconductor laser or a gas laser. The wavelength of the laser light emitted from the light source 10 is, for example, 350 nm or more and 1,000 nm or less. The half mirror 2, for example, reflects the laser light and transmits Raman scattered light from the sensor chip 30 therethrough. In place of the half mirror 2, a dichroic mirror may be used. The lens 4 is, for example, a condenser lens which condenses the laser light on the sensor chip 30.

The light-blocking filter 20 can block the laser light emitted from the light source 10. The laser light is not irradiated on the sensor chip 30 in a state where the light-blocking filter 20 is disposed on the optical axis of the laser light. Here, the "optical axis of the laser light" refers to a path through which the laser light passes in the case where the laser light is emitted from the light source 10. The light-blocking filter 20 may be in the shape of a plate or a film. The material of the light-blocking filter 20 is not particularly limited as long as the light-blocking filter 20 can block the laser light emitted from the light source 10.

The light-blocking filter moving section 22 moves the light-blocking filter 20. The light-blocking filter moving section 22 movably supports the light-blocking filter 20. The light-blocking filter moving section 22 includes, for example, a support section which supports the light-blocking filter 20 and a driving section which moves the support section, and can move the light-blocking filter 20 by driving the driving section in response to a signal from the processing section 80 thereby moving the support section. The driving section of the light-blocking filter moving section 22 is, for example, a motor. The light-blocking filter moving section 22 may be configured to include a knob so that the support section which supports the light-blocking filter 20 is moved manually by holding the knob.

The sensor chip 30 releases Raman scattered light by receiving the laser light. The sensor chip 30 is a sensor chip for surface-enhanced Raman scattering (SERS) having an organic molecular modification film. The sensor chip 30 has a first region 30a and a second region 30b. The regions 30a and 30b are each a surface including an organic molecular modification film of the sensor chip 30 and are regions different from each other. A detailed description of the sensor chip 30 will be made later.

The irradiation region changing section 32 changes a region to be irradiated with the laser light (a laser light irradiation region) in the sensor chip 30. Specifically, the irradiation region changing section 32 changes the laser light irradiation region by moving the sensor chip 30. The irradiation region changing section 32 movably supports the sensor chip 30. The irradiation region changing section 32, for example, changes the optical axis of the laser light in the sensor chip 30. The irradiation region changing section 32 includes, for example, a support section which supports the sensor chip 30 and a driving section which moves the support section, and can move the sensor chip 30 by driving the driving section in response to a signal from the processing section 80 thereby moving the support section. The driving section of the irradiation region changing section 32 is, for example, a motor. The irradiation region changing section 32 may be configured to include a knob so that the support section which supports the sensor chip 30 is moved manually by holding the knob.

The irradiation region changing section 32 may change the laser light irradiation region by moving not the sensor chip 30, but the light source 10 as long as the region to be irradiated with the laser light in the sensor chip 30 can be changed. Further, the irradiation region changing section 32 may change the laser light irradiation region by changing the placement of the half mirror 2 or the lens 4. Further, the irradiation region changing section 32 may change the laser light irradiation region by changing the angle at which the laser light is emitted.

In the flow path 40, a gas (gas sample) containing a target substance to be detected flows. In the flow path 40, the sensor chip 30 is supported. When a pump 41 provided in the flow path 40 is driven, the inside of the flow path 40 is brought into a negative pressure, and therefore, the gas containing the target substance is sucked from a suction port 42. The gas sucked from the suction port 42 passes in the vicinity of the surface of the sensor chip 30 and is discharged from a discharge port 43. When the gas passes in the vicinity of the surface of the sensor chip 30, the target substance is adsorbed in the vicinity of the surface of the sensor chip 30. Specifically, the target substance to be detected is nitrogen monoxide (NO), and the first gas flowing in the flow path 40 may be a gas containing the breath of an asthma patient or the like and the air or may be a nitrogen monoxide (NO) gas.

The light detector 50 detects Raman scattered light from the sensor chip 30 by irradiation with the laser light. The Raman scattered light released in the sensor chip 30 passes through the lens 4, the half mirror 2, a Rayleigh cut filter 6, and a lens 8, and then reaches the light detector 50. The Raman scattered light released in the sensor chip 30 contains Rayleigh scattered light with the same wavelength as that of the laser light emitted from the light source 10, and the Rayleigh scattered light can be removed by the Rayleigh cut filter 6. The lens 8 is, for example, a condenser lens which condenses the Raman scattered light on the light detector 50.

The light detector 50 has a spectroscope 52 and a light-receiving element 54. The spectroscope 52 is, for example, formed from an etalon or the like utilizing Fabry-Perot resonation, and can make a pass wavelength band variable. The light-receiving element 54 receives Raman scattered light having passed through the spectroscope 52. The light-receiving element 54 is, for example, a photodiode. The light detector 50 sends information regarding the intensity of light received by the light-receiving element 54 to the processing section 80 through the control section 60.

Figure 2:
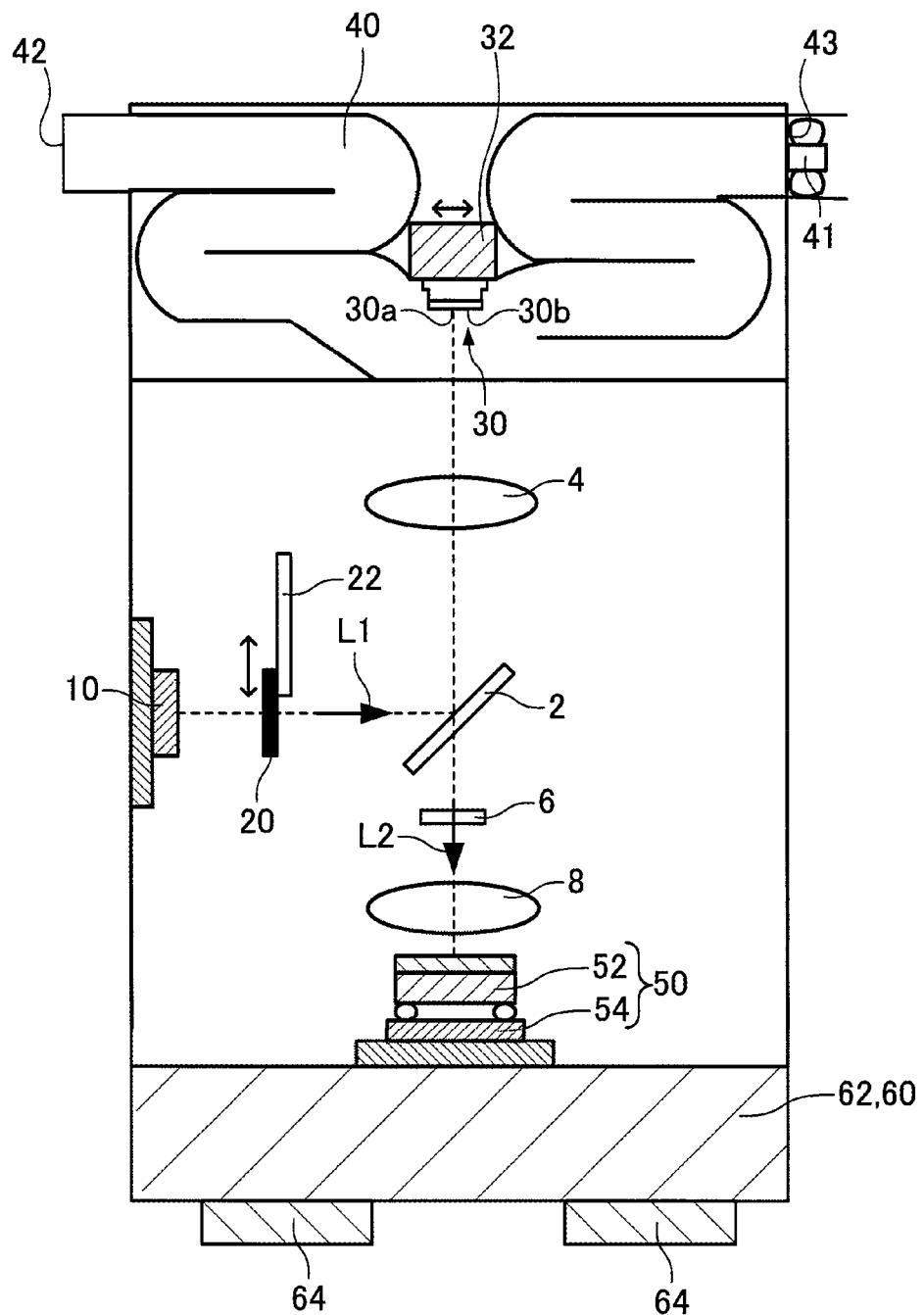
FIG. 2 is a view schematically showing the substance detection device according to the first embodiment.

The control section 60 controls the light-blocking filter moving section 22, the irradiation region changing section 32, and the pump 41 in response to a signal from the processing section 80. The control section 60 may be configured such that it is realized by a dedicated circuit so as to perform the above-mentioned control. Further, the control section 60 may be configured such that it functions as a computer by, for example, allowing a CPU (central processing unit) to execute a control program stored in a memory device such as a ROM (read only memory) or a RAM (random access memory) so as to perform the above-mentioned control. The control section 60 may be housed in a housing section 62 provided below the light detector 50 as shown in FIG. 2. The control section 60 may be electrically connected to an external terminal 64 as shown in FIG. 2. Incidentally, in FIG. 2, the illustration of the control section 60, the operation section 70, the display section 72, the memory section 74, the memory medium 76, and the processing section 80 is omitted for the sake of convenience.

As shown in FIG. 1, the operation section 70 acquires an operation signal in accordance with the operation by a user and performs processing of sending the signal to the processing section 80. The operation section 70 is, for example, a button, a key, a touch panel display, a microphone, or the like.

The display section 72 displays the processing result or the like of the processing section 80 based on a display signal input from the processing section 80. The display section 72 is, for example, a liquid crystal display (LCD), a cathode ray tube (CRT), a touch panel display, or the like.

The memory section 74 stores a program for allowing the processing section 80 to perform a variety of calculation processing and control processing, data, and the like. The memory section 74 is further used as a working region for the processing section 80, and temporarily stores an operation signal input from the operation section 70, a program or data read from the memory medium 76, the results of calculation performed according to a variety of programs by the processing section 80, and the like. In the memory section 74, a database 75 is stored.

In the database 75, data on a target substance to be analyzed are registered. Specifically, in the database 75, data for specifying (qualitatively determining) the target substance from a Raman shift, and data for specifying (qualitatively determining) the concentration of the target substance from the intensity of a Raman spectrum are registered. The database 75 may be stored in the memory medium 76.

The memory medium 76 is a computer readable memory medium for storing a variety of application programs and data. The programs may be delivered to the memory medium 76 (memory section 74) through a network or the like from an information memory medium included in a host device (server). The memory medium 76 may also function as a memory section which stores data required to be stored for a long period of time among the data generated by the processing of the processing section 80. The memory medium 76 is realized by, for example, an optical disk (CD, DVD), an optical magnetic disk (MO), a magnetic disk, a hard disk, a magnetic tape, or a memory (ROM, flash memory, or the like).

The processing section 80 performs a variety of calculation processing according to a program stored in the memory section 74 or a program stored in the memory medium 76. In this embodiment, the processing section 80 functions as a laser irradiation processing section 81, a first light intensity acquisition section 82, a first concentration calculation section 83, and an irradiation region changing processing section 84 by performing a program stored in the memory section 74. The functions of the processing section 80 can be realized by hardware such as a variety of processors (CPU, DSP, etc.) and ASIC (a gate array, etc.), and programs. Incidentally, at least part of the functions of the processing section 80 may be realized by hardware (dedicated circuit).

The laser irradiation processing section 81 performs processing of irradiating the first region 30a of the sensor chip 30 with the laser light. Specifically, the laser irradiation processing section 81 performs processing of removing the light-blocking filter 20 from the optical axis of the laser light by controlling the light-blocking filter moving section 22 and irradiating the first region 30a of the sensor chip 30 with the laser light based on the timing of starting the pump 41 (for example, after 30 seconds from when the pump 41 is moved). The moving distance of the light-blocking filter 20 by the processing of the processing section 80 is, for example, about 100 μm.

Figure 3:
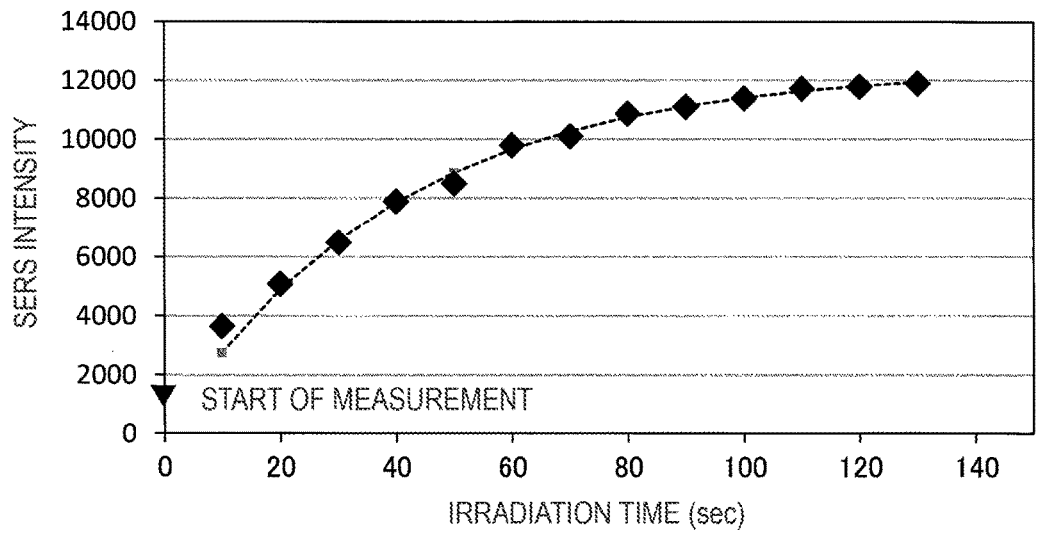
FIG. 3 is a graph showing a relationship between a laser light irradiation time and an SERS intensity.

The first light intensity acquisition section 82 performs first measurement processing by acquiring the intensity of Raman scattered light from the first region 30a of the sensor chip 30 exposed to the first gas detected by the light detector 50. Here, FIG. 3 is a graph showing a relationship between a laser light irradiation time for the sensor chip and an SERS intensity (the intensity of Raman scattered light). Specifically, FIG. 3 shows a relationship between a laser light irradiation time and an SERS intensity when an NO (nitrogen monoxide) gas at 20 ppm is used as the first gas to which the sensor chip 30 is exposed, and the wavelength of the laser light is set to 632 nm, and the intensity of the laser light is set to 0.5 mW.

The first light intensity acquisition section 82, for example as shown in FIG. 3, acquires the intensity of Raman scattered light a plurality of times at predetermined intervals based on the timing of irradiation of the first region 30a of the sensor chip 30 with the laser light in the first measurement processing. Specifically, the first light intensity acquisition section 82 starts the first measurement processing at the same time that the laser irradiation processing section 81 completes the processing of removing the light-blocking filter 20 from the optical axis of the laser light by controlling the light-blocking filter moving section 22. In the example shown in FIG. 3, the first light intensity acquisition section 82 acquires the SERS intensity at 605 cm$^{-1}$ 13 times in total at every 10 seconds from when the first measurement processing is started, and after the 13$^{th}$ acquisition of the SERS intensity, the first measurement processing is completed.

The first concentration calculation section 83 calculates the concentration of the target substance in the first gas based on the measurement result of the first measurement processing performed by the first light intensity acquisition section 82. Specifically, the first concentration calculation section 83 performs fitting based on the measurement result of the first measurement processing and calculates the saturation intensity (predicted saturation intensity) of Raman scattered light. Here, when a Langmuir adsorption model is used, the coverage θ of the surface of the sensor chip at a certain time t can be represented by the following formula (1). In the following formula (1), A represents a coefficient.

$$\theta = 1 - \exp(-At) \quad (1)$$

In the formula of the SERS signal intensity, the SERS signal intensity can be regarded to be proportional to the coverage when the coverage is low, and therefore, the SERS intensity (Raman scattered light intensity) $I_{SERS}$ can be represented by the following formula (2). In the following formula (2), B represents a coefficient.

$$ISERS = B\theta = B[1 - \exp(-At)] \quad (2)$$

The first concentration calculation section 83, for example as shown in FIG. 3, determines A and B in the formulae (1) and (2) by fitting using an algorithm such that the value of a squared difference between the SERS intensity obtained 13 times in total at every 10 seconds from when the first measurement processing is started and the value of the formula (2) at each time is minimized (see the broken line in FIG. 3). B represents the predicted saturation intensity, and the first concentration calculation section 83 calculates the concentration of NO by comparing the determined B with the data of the calibration curve of the SERS intensity and the concentration of NO (the concentration of the target substance) stored in advance in the memory section 74. The processing section 80 performs processing of displaying the calculated concentration of NO in the display section 72.

The first light intensity acquisition section 82 may acquire the intensity of Raman scattered light only once after waiting until the intensity of Raman scattered light is saturated from the irradiation of the first region of the sensor chip 30 with the laser light (for example, about 5 minutes). In this case, the first concentration calculation section 83 may calculate the concentration of NO by comparison with the data of the calibration curve of the intensity of Raman scattered light acquired by the first light intensity acquisition section 82 and the concentration of NO without performing fitting as described above.

The irradiation region changing processing section performs processing of blocking the laser light by controlling the light-blocking filter moving section 22 after the first measurement processing and adjusting the laser light irradiation region from the first region 30a to the second region 30b of the sensor chip 30 by controlling the irradiation region changing section 32. The moving distance of the sensor chip 30 (for example, a distance between the first region and the second region) by the processing of the processing section 80 is, for example, 5 μm or more and 5 mm or less, preferably 10 μm or more and 1 mm or less, more preferably 100 μm or more and 1 mm or less. The size of the sensor chip 30 is 3 mm square or more and 5 mm square or less from the viewpoint of ease of handling, and when the moving distance is 1 mm, it is possible to perform measurement 9 times to 25 times in one sensor chip 30. Therefore, by setting the moving distance to 1 mm or less, the number of measurements in one sensor chip 30 can be increased. When the moving distance is less than 100 μm, the cost of the driving section of the irradiation region changing section 32 is increased (a driving section using, for example, an expensive MEMS is needed). Further, it is necessary to set the moving distance to be larger than the focal size (spot diameter) Φ in the sensor chip 30 of the laser light emitted from the light source 10. For example, when the wavelength of the laser light is represented by λ, and the numerical aperture of the lens 4 is represented by NA, the following relationship is satisfied: Φ=1.22λ/NA, and when NA is set to 0.2 and λ is set to 632 nm, Φ is about 3.8 μm.

Figure 4:
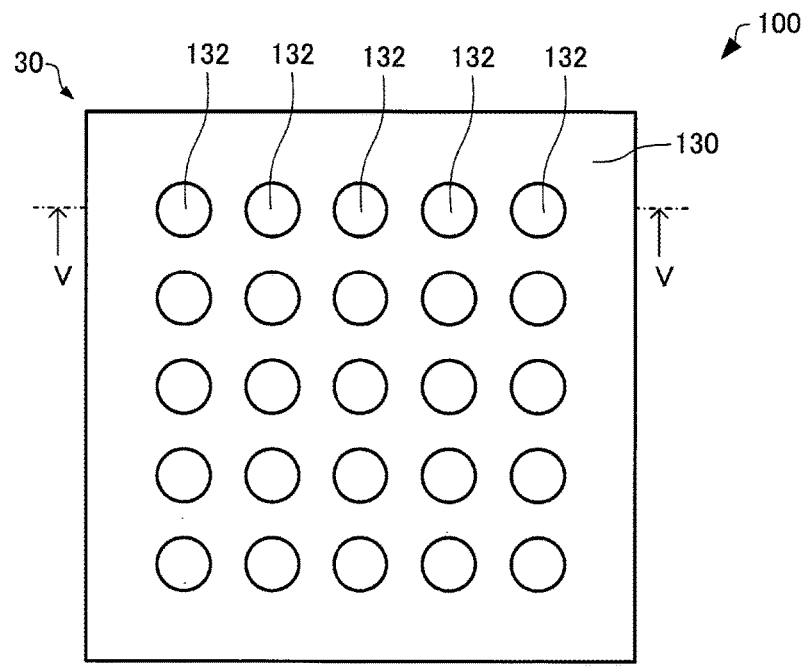
FIG. 4 is a plan view schematically showing a sensor chip according to the first embodiment.
Figure 5:
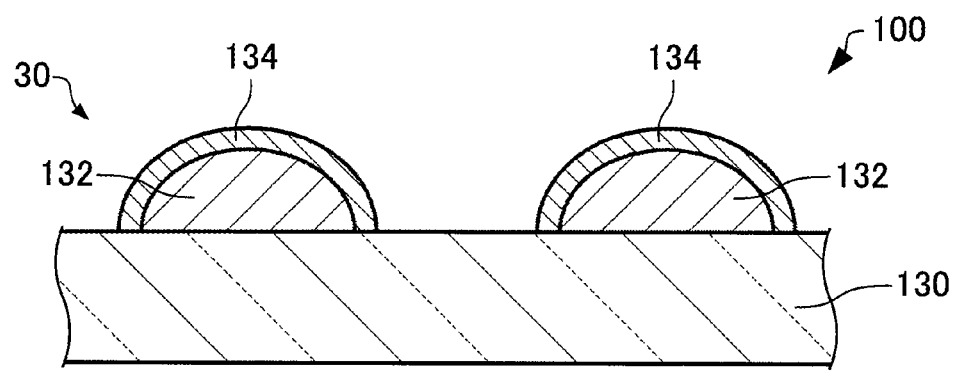
FIG. 5 is a cross-sectional view schematically showing the sensor chip according to the first embodiment.

Next, the sensor chip 30 will be described in detail. FIG. 4 is a plan view schematically showing the sensor chip 30. FIG. 5 is a cross-sectional view taken along the line V-V in FIG. 4 schematically showing the sensor chip 30.

As shown in FIGS. 4 and 5, the sensor chip 30 includes a substrate 130, a metal microstructure 132, and an organic molecular modification film 134. Incidentally, in FIG. 4, the illustration of the organic molecular modification film 134 is omitted for the sake of convenience.

The substrate 130 is, for example, a glass substrate, a silicon substrate, or a resin substrate.

The metal microstructure 132 is provided on the substrate 130. The shape of the metal microstructure 132 is not particularly limited, and is, for example, a cylinder, a particle, a prism, a sphere, or a spheroid. The size (for example, the diameter) of the metal microstructure 132 is equal to or smaller than the wavelength of the light irradiated on the sensor chip 30. Specifically, the size of the metal microstructure 132 is 40 nm or more and 700 nm or less. In the example shown in the drawing, a plurality of metal microstructures 132 are provided. The material of the metal microstructure 132 is, for example, gold, silver, aluminum, or copper. The metal microstructure 132 is formed by, for example, a vacuum deposition method or the like.

When the metal microstructure 132 is irradiated with light, surface plasmon resonance (SPR) occurs. Specifically, in the metal microstructure 132, localized surface plasmon resonance (LSPR) occurs. LSPR is a phenomenon in which when light is incident on a metal structure with a size equal to or smaller than the wavelength of the light, free electrons present in the metal collectively oscillate due to an electric field component of the light, and a local electric field is induced outside. By this local electric field, Raman scattered light can be enhanced. A phenomenon in which Raman scattered light is enhanced by an electric field induced by SPR in this manner is referred to as "electric field enhancement effect". The intensity of Raman scattered light enhanced by SPR (SERS light) is proportional to the fourth power of the electric field enhanced by SPR.

The organic molecular modification film 134 is provided on the metal microstructure 132. The organic molecular modification film 134 includes a modifying molecule according to this embodiment (hereinafter also simply referred to as "modifying molecule"). The modifying molecule is disposed on the surface of the metal microstructure 132. The organic molecular modification film 134 is formed by, for example, immersing the substrate 130 having the metal microstructure 132 formed thereon in a solution in which the modifying molecule is diluted (for example, at a concentration of 1 mM) for a predetermined time or more (for example, 24 hours), and thereafter, taking out the substrate 130 from the solution and blowing off the solvent.

Figure 6:
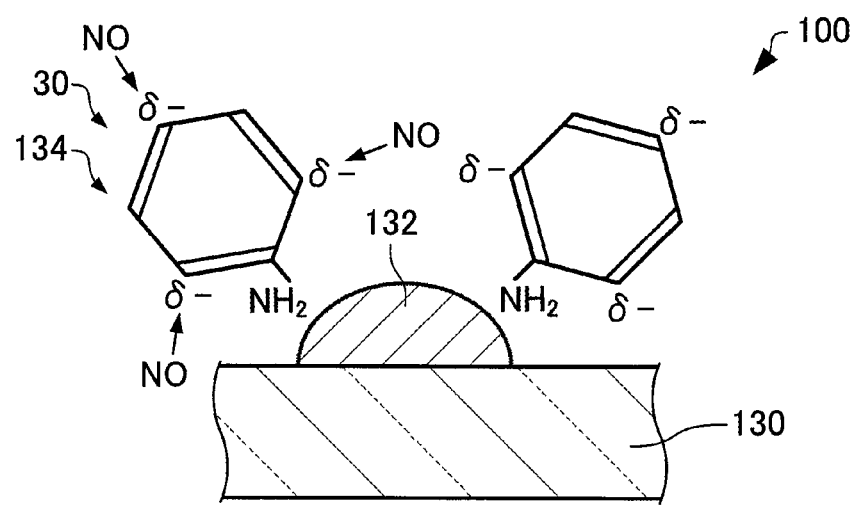
FIG. 6 is a cross-sectional view schematically showing the sensor chip according to the first embodiment.

The modifying molecule is derived from, for example, a compound having an amine-based functional group. Specifically, the modifying molecule is derived from aniline which is a benzene ring having an amine group (see the following formula (3)). In this case, the modifying molecule binds to the metal microstructure 132 through the amine group as shown in FIG. 6. According to this, the organic molecular modification film 134 can modify the metal microstructure 132. It is considered that NO (nitrogen monoxide) reacts with oxygen in the air and is converted to $N_2O_3$ as a reactant, and $N_2O_3$ having an electron-withdrawing property reacts with the benzene ring at an electron localization site (a site denoted by δ—shown in FIG. 6). In this manner, the sensor chip 30 can trap NO.

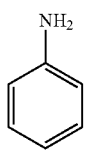

(3)

The modifying molecule is not limited to the amine-based functional group. The modifying molecule may be derived from a compound having a sulfur-based functional group, for example, methanethiol ($CH_3SH$). Here, the phrase "derived from a given compound (for example, aniline or methanethiol)" refers to that the compound is bound to the metal microstructure 132 through a bond such as a coordinate bond, a covalent bond, an ionic bond, or a hydrogen bond as it is or by detaching part of a substituent, whereby the modifying molecule is obtained.

The substance detection device 100 has, for example, the following characteristics.

The substance detection device 100 includes the light-blocking filter 20 capable of blocking laser light emitted from the light source 10, the light-blocking filter moving section 22 which moves the light-blocking filter 20, and the irradiation region changing section 32 which changes a laser light irradiation region in the sensor chip 30. Therefore, in the substance detection device 100, after the measurement (first measurement) regarding the intensity of Raman scattered light detected by the light detector 50 is completed, the laser light irradiation region in the sensor chip 30 can be changed in a state where the laser light is blocked. Due to this, in the subsequent measurement, a region of the sensor chip 30 which is not yet irradiated with laser light is irradiated with laser light and Raman scattered light can be detected. Therefore, in the substance detection device 100, the deterioration of the organic molecular modification film 134 of the sensor chip 30 by the laser light can be suppressed. As a result, in the substance detection device 100, a target substance can be detected with high sensitivity. As shown in the below-mentioned experimental example, the organic molecular modification film 134 is deteriorated by irradiation with laser light.

In the substance detection device 100, the irradiation region changing section 32 changes the laser light irradiation region by moving the sensor chip 30. Due to this, in the substance detection device 100, the irradiation region can be easily changed as compared with the case where the laser light irradiation region is changed by moving the light source 10 or changing the placement of the lens 4 or the like. For example, in the case where the light source 10 is moved, the irradiation region changing section 32 which can move a heavier member may be needed in some cases, and in the case where the placement of the lens 4 or the half mirror 2 is changed, the irradiation region changing section 32 which enables finer adjustment when moving the member may be needed in some cases.

The substance detection device 100 includes the irradiation region changing processing section 84 which performs processing of blocking the laser light by controlling the light-blocking filter moving section 22 after the first measurement processing and adjusting the laser light irradiation region from the first region 30a to the second region 30b of the sensor chip 30 by controlling the irradiation region changing section 32. Due to this, in the substance detection device 100, after the measurement (first measurement) regarding the intensity of Raman scattered light detected by the light detector 50 is completed, the laser light irradiation region in the sensor chip 30 can be changed in a state where the laser light is blocked by the irradiation region changing processing section 84.

In the substance detection device 100, the first light intensity acquisition section 82 acquires the intensity of Raman scattered light a plurality of times at predetermined intervals based on the timing of irradiation of the first region 30a in the first measurement processing. Due to this, in the substance detection device 100, a predicted saturation intensity is determined before the intensity of Raman scattered light is brought into a saturated state, and based on the predicted saturation intensity, the concentration of a target substance can be calculated. Therefore, in the substance detection device 100, it is not necessary to wait until the intensity of Raman scattered light is brought into a saturated state, and thus, a time until the concentration of a target substance is calculated can be reduced.

In the substance detection device 100, the organic molecular modification film 134 of the sensor chip 30 is derived from a compound having an amine-based or sulfur-based functional group. Due to this, in the substance detection device 100, NO can be detected with high sensitivity. Here, an NO gas has attracted attention from the following two aspects: air pollution and medical treatment. With respect to the former aspect, $NO_x$ which is a byproduct produced in a large amount from anthropogenic activity associated with a combustion system is involved in the production of acid rain, and therefore leads to environmental problems. With respect to the medical treatment, an NO gas has been recognized as a biomarker accompanying airway inflammation if the concentration thereof is on the order of ppb, and if the concentration thereof is on the order of ppm, an NO gas has been used as, for example, a drug because it has a vasodilation effect. In this manner, the measurement of the concentration of NO has a need in terms of environmental problems and medical treatment. When NO is tried to be detected directly by SERS, the types of molecular vibration are few because NO is a simple two-atom molecule, and also the intensity is low. Therefore, detection at trace concentration not higher than 1 percent such as a concentration on the order of ppb or ppm is not easy. Therefore, in the substance detection device 100, NO can be detected with high sensitivity by trapping No using the organic molecular modification film 134.

1.2. Substance Detection Method

Figure 7:
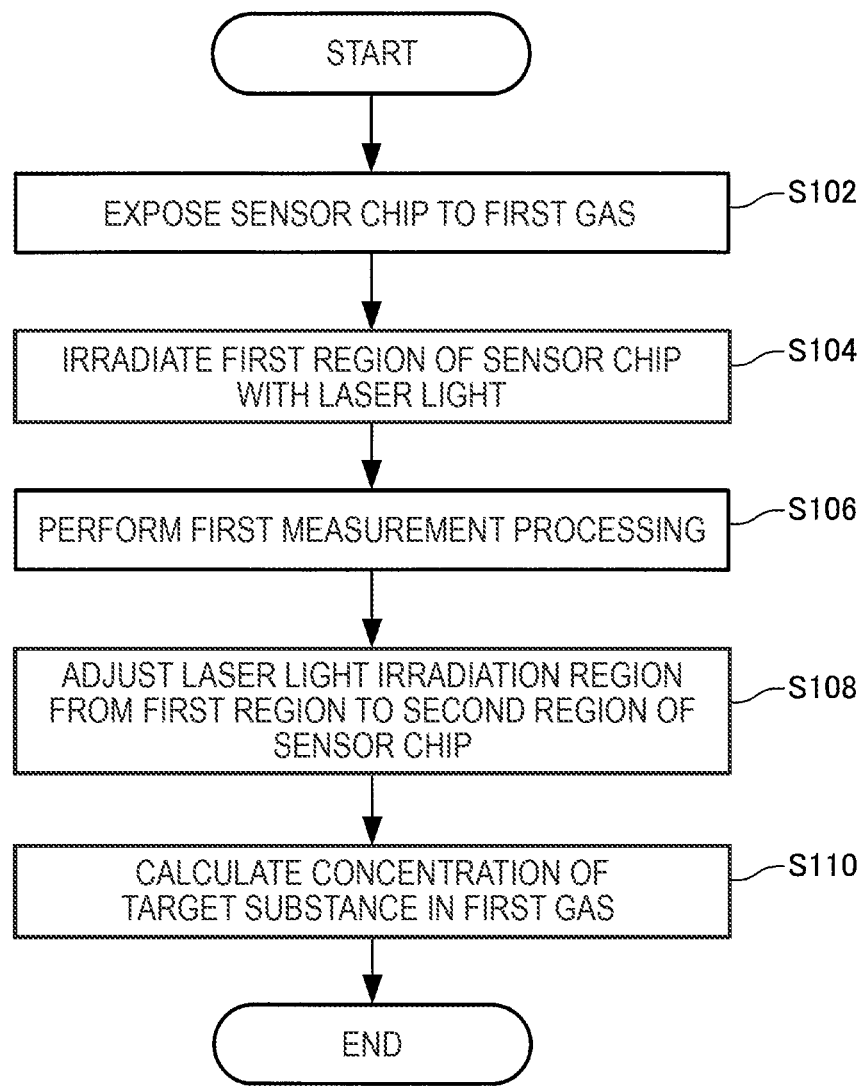
FIG. 7 is a flowchart for explaining a substance detection method according to a first embodiment.

Next, a substance detection method according to a first embodiment will be described with reference to the drawings. FIG. 7 is a flowchart for explaining the substance detection method according to the first embodiment. Hereinafter, a detection method using the substance detection device 100 will be described as the substance detection method according to the first embodiment.

For example, when a user requests processing for determining the concentration of a target substance through the operation section 70, the processing section 80 starts the processing in response to an operation signal from the operation section 70. For example, the user inputs the type of the target substance to be analyzed (to be detected) when requesting the processing.

First, the processing section 80 performs processing of exposing the sensor chip 30 to a first gas (for example, an NO gas) (S102). Specifically, the processing section 80 performs processing of driving the pump 41 in response to an operation signal from the operation section 70. By doing this, the NO gas flows in the flow path 40, and therefore, the sensor chip 30 can be exposed to the NO gas.

Subsequently, the laser irradiation processing section 81 performs processing of irradiating the first region 30a of the sensor chip 30 exposed to the NO gas with laser light (first laser light) (S104). Specifically, the laser irradiation processing section 81 removes the light-blocking filter 20 from the optical axis of the laser light by controlling the light-blocking filter moving section 22 after a predetermined time (for example, after 30 seconds) has elapsed from when the pump 41 is driven. By doing this, the first region 30a is irradiated with the laser light.

Subsequently, the first light intensity acquisition section 82 performs first measurement processing by acquiring the intensity of Raman scattered light from the first region 30a of the sensor chip 30 detected by the light detector 50 (S106). Specifically, the first light intensity acquisition section 82 acquires the intensity of Raman scattered light a plurality of times at predetermined intervals based on the timing of irradiation of the first region 30a. For example, the first light intensity acquisition section 82 starts the first measurement processing at the same time that the laser irradiation processing section 81 completes the processing of removing the light-blocking filter 20 from the optical axis of the laser light by controlling the light-blocking filter moving section 22.

Subsequently, the irradiation region changing processing section 84 moves the light-blocking filter 20 to the optical axis of the laser light and blocks the laser light by controlling the light-blocking filter moving section 22 after the first measurement processing (for example, in response to a signal of completion of the first measurement from the first light intensity acquisition section 82). After blocking the laser light, the irradiation region changing processing section 84 performs processing of moving the sensor chip 30 and adjusting the optical axis of the laser light (the irradiation region where the sensor chip 30 is irradiated with the laser light) from the first region 30a to the second region 30b of the sensor chip 30 by controlling the irradiation region changing section 32 (S108).

Subsequently, the first concentration calculation section 83 calculates the concentration of the target substance (NO) in the NO gas based on the measurement result of the first measurement processing performed by the first light intensity acquisition section 82 (S110). Then, the processing section 80 outputs a signal for displaying the concentration of NO in the display section 72, and the processing is completed. Incidentally, the processing of calculating the concentration of NO in the NO gas (S110) may be performed after the first measurement processing (S106) and before the processing of adjusting the laser light irradiation region from the first region 30a to the second region 30b (S108).

In the case where, for example, the concentration of NO in the same NO gas is determined again after completion of the processing, the processing of (S104), (S106) and (S110) can be performed by irradiating the second region 30b of the sensor chip 30 (in the processing of (S104), the "first region 30a" is replaced by the "second region 30b") after the sensor chip is exposed to the same NO gas. Further, in the case where the concentration of NO in another NO gas is determined, the processing can be performed in the same manner as described above after the sensor chip is exposed to another NO gas.

In the substance detection method according to the first embodiment, a target substance can be detected with high sensitivity as described in "1.1. Substance Detection Device".

1.3. Experimental Example

The invention will be more specifically described by showing an experimental example below. Incidentally, the invention is by no means limited to the following experimental example.

1.3.1. Deterioration of Organic Molecular Modification Film by Irradiation with Light A sensor chip including an organic molecular modification film containing a modifying molecule (a modifying molecule derived from a compound having an amine-based or sulfur-based functional group) as the sensor chip 30 was irradiated with laser light for a predetermined time, and deterioration of the organic molecular modification film by irradiation with light was examined. As the material of a metal microstructure of the sensor chip, gold was used.

Figure 8:
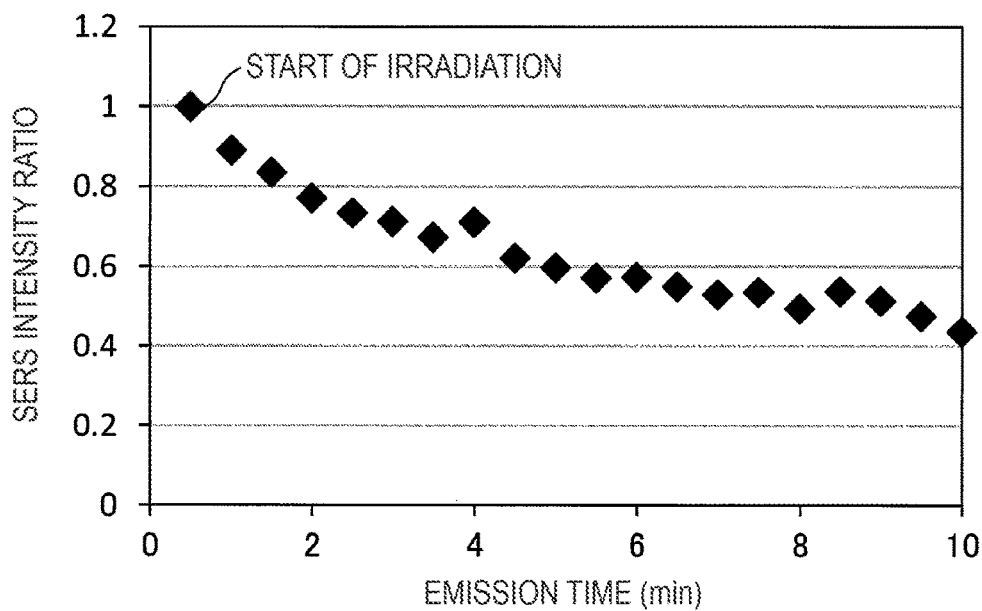
FIG. 8 is a graph showing a relationship between a laser light emission time and an SERS intensity ratio.
Figure 9:
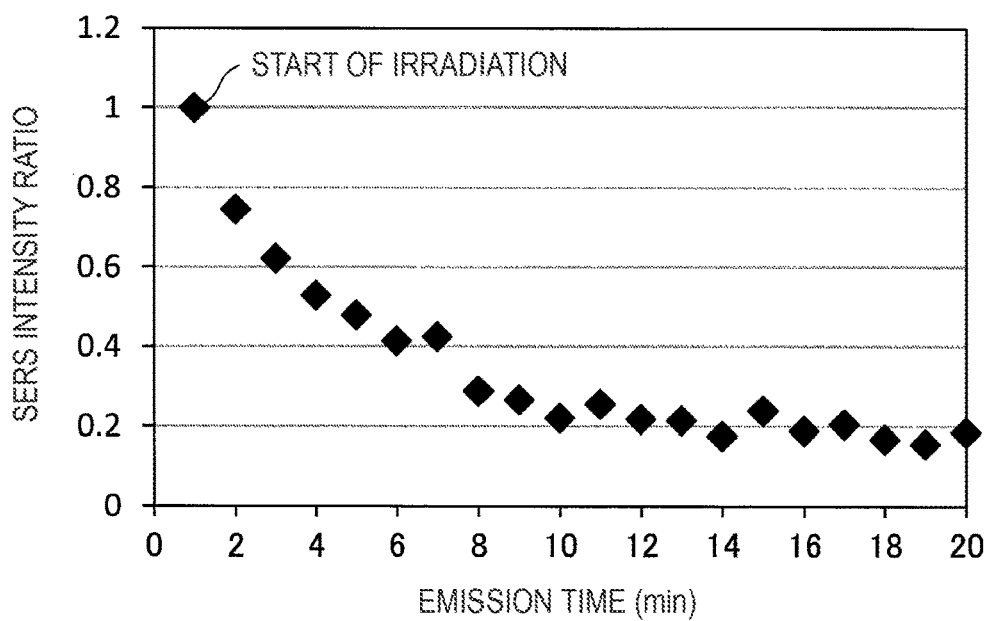
FIG. 9 is a graph showing a relationship between a laser light emission time and an SERS intensity ratio.
Figure 10:
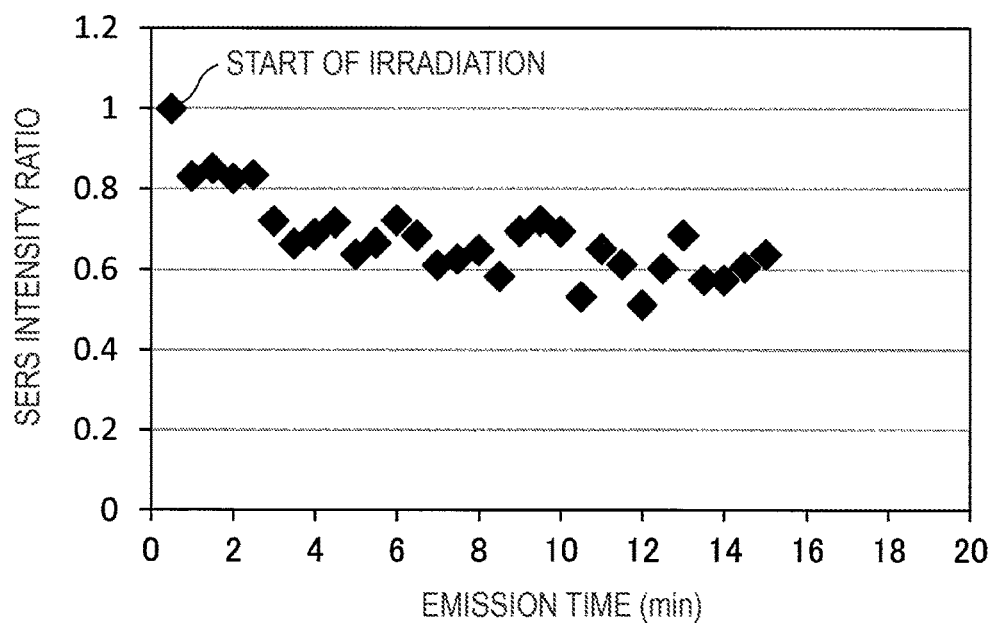
FIG. 10 is a graph showing a relationship between a laser light emission time and an SERS intensity ratio.
Figure 11:
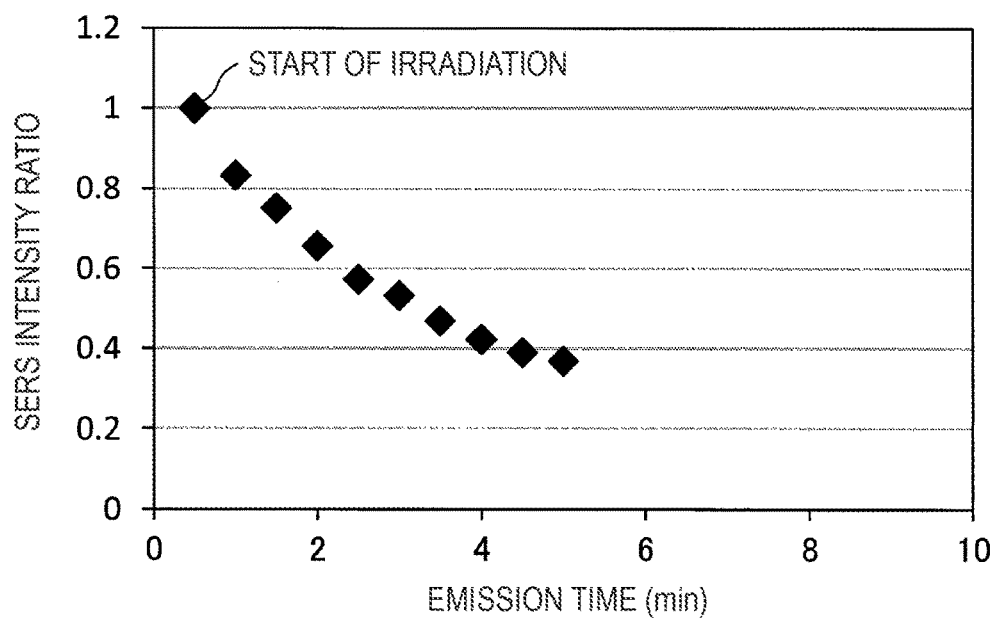
FIG. 11 is a graph showing a relationship between a laser light emission time and an SERS intensity ratio.

FIGS. 8 to 11 are graphs each showing a relationship between a laser light emission time and an SERS intensity ratio in a sensor chip including an organic molecular modification film containing a modifying molecule. In FIGS. 8 to 11, the horizontal axis represents an elapsed time from when laser light started to be emitted from the light source, and each sensor chip was irradiated with laser light from the time of "start of irradiation" shown in each graph. In FIGS. 8 to 11, the vertical axis represents a standardized intensity of Raman scattered light (SERS intensity ratio) when the initial plot (a plot obtained at the shortest irradiation time) was taken as 1. In FIG. 8, the modifying molecule is derived from ammonia ($NH_3$). In FIG. 9, the modifying molecule is derived from aniline. In FIG. 10, the modifying molecule is derived from DAR-4M (see the following formula (4)). In FIG. 11, the modifying molecule is derived from dimethyl sulfide (see the following formula (5)).

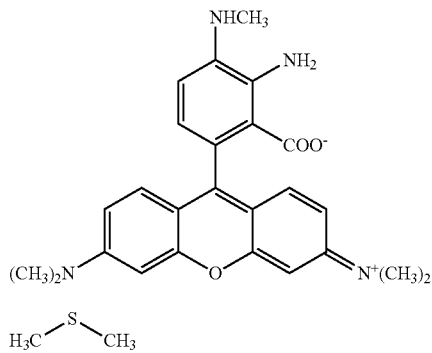

(4)

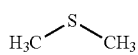

(5)

In FIGS. 8 to 10, laser light with a wavelength of 632 nm and an intensity of 0.5 mW was irradiated. In FIG. 11, laser light with a wavelength of 632 nm and an intensity of 0.2 mW was irradiated.

From FIGS. 8 to 11, it was found that when an organic molecular modification film containing a modifying molecule derived from a compound having an amine-based or sulfur-based functional group is irradiated with laser light, as the irradiation time elapses, the intensity of Raman scattered light due to the organic molecular modification film (the peak intensity of the Raman spectrum) decreases. This is because by irradiation with laser light, in the case of the organic molecular modification film containing a modifying molecule derived from a compound having an amine-based functional group, the organic molecular modification film reacts with the light and is deteriorated, and in the case of the organic molecular modification film containing a modifying molecule derived from a compound having a sulfur-based functional group, the organic molecular modification film is detached by the light.

1.3.2. Mechanism of NO Trapping by Organic Molecular Modification Film

By using a sensor chip including an organic molecular modification film containing a modifying molecule derived from aniline, the mechanism of NO trapping by the organic molecular modification film was examined.

Figure 12:
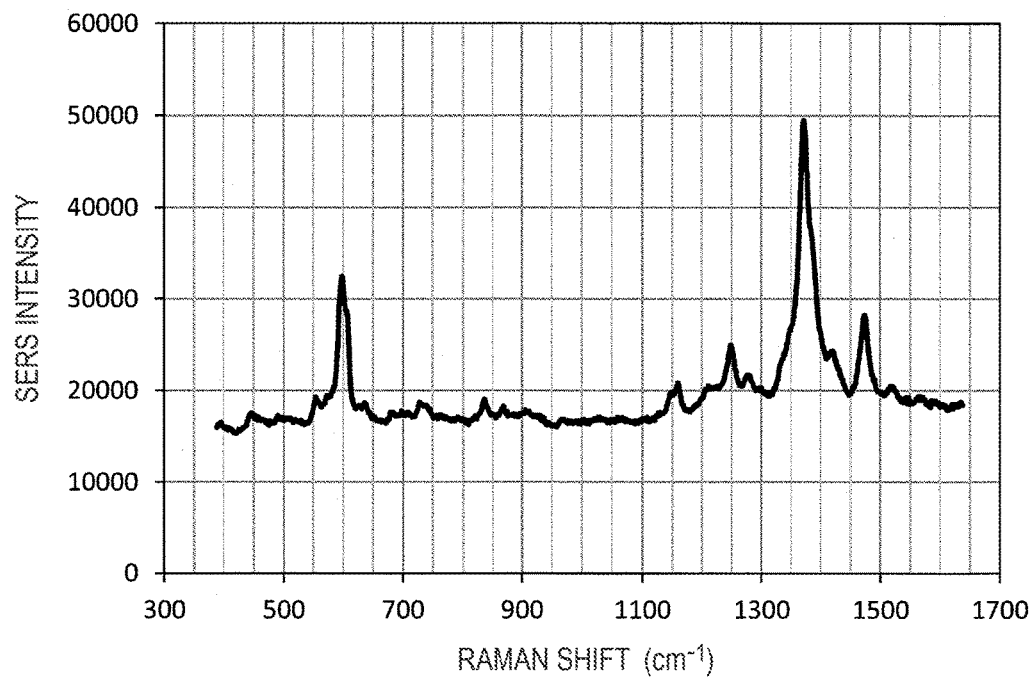
FIG. 12 shows an SERS spectrum.

FIG. 12 shows an SERS spectrum of a difference between before and after exposure (a value obtained by subtracting the SERS intensity before exposure from the SERS intensity after exposure) when a sensor chip which includes the organic molecular modification film 134 containing a modifying molecule derived from aniline and in which the material of the metal microstructure 132 is gold was exposed to a gas containing NO at 20 ppm. Laser light with a wavelength of 632 nm and an intensity of 0.5 mW was irradiated. As shown in FIG. 12, strong peaks were confirmed at 605 $cm^{-1}$ and 1374 $cm^{-1}$. This coincides with a frequency band derived from an $NO_2$ group (nitro group), and therefore, it is considered that the sensor chip reacted with and trapped NO in the NO gas and nitroaniline was produced.

Figure 13:
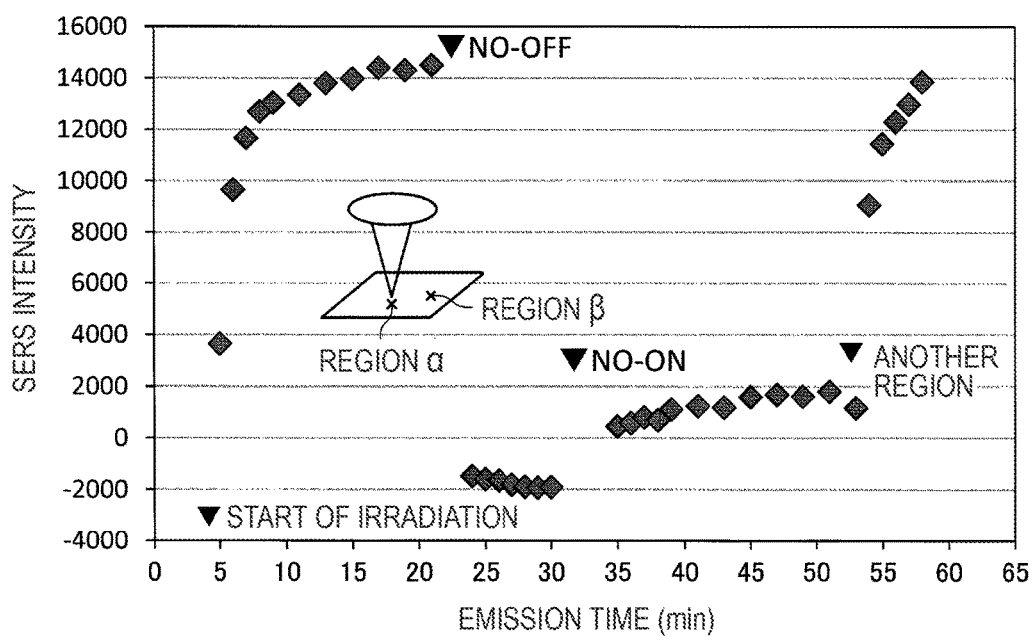
FIG. 13 is a graph showing a relationship between a laser light emission time and an SERS intensity.

Subsequently, by focusing on the peak at 605 $cm^{-1}$, an experiment as shown below was performed. FIG. 13 is a graph showing a relationship between a laser light emission time and a Raman scattered light intensity in a sensor chip including an organic molecular modification film containing a modifying molecule derived from aniline.

First, as shown in FIG. 13, the sensor chip was exposed to an NO gas, and after 5 minutes from when laser light was emitted, a region α of the sensor chip was irradiated with the laser light (first step). The SERS intensity derived from NO gradually increased (see after an emission time of 5 minutes to 20 minutes).

Subsequently, the exposure of the sensor chip to the NO gas was stopped (second step). The SERS intensity derived from NO gradually decreased (see after an emission time of 23 minutes to 30 minutes). This is because the organic molecular modification film promptly releases NO and light deterioration of the organic molecular modification film started.

Subsequently, the sensor chip was exposed to the NO gas again (third step). The SERS intensity derived from NO was significantly smaller than the SERS intensity obtained in the first step (see after an emission time of 35 minutes to 53 minutes). It was found that the NO trapping property of the organic molecular modification film is lost and the detection sensitivity is significantly decreased in a region where light deterioration occurred in the organic molecular modification film.

Subsequently, the optical axis of the laser light (laser light irradiation region) was moved from the region α to a region β of the sensor chip (fourth step). The SERS intensity derived from NO gradually increased in the same manner as the first step (see after an emission time of 55 minutes to 58 minutes). It was found that the SERS intensity increases immediately after irradiation with the laser light during exposure to the NO gas.

From the experiment including the first to fourth steps, the following (a), (b), and (c) were found.

(a) The trapping of NO by the organic molecular modification film starts with the light irradiation as the starting point (see the first and fourth steps).

(b) When the exposure to NO is stopped, the organic molecular modification film promptly releases NO (see the second step).

(c) The NO trapping property of the organic molecular modification film is lost and the detection sensitivity is significantly decreased in a region where light deterioration occurred in the organic molecular modification film (see the third step).

By utilizing the characteristics of the sensor chip as described above, for example, in the substance detection device 100, NO is detected. The characteristics of the sensor chip as described above are considered to be resulted from a photochemical reaction due to light enormously enhanced by 100,000 to 1,000,000,000 times formed extremely locally (LSPR) in a nanometer-scale metal microstructure, and are considered to be a response specific to an SERS sensor chip (a sensor chip including a metal microstructure).

2. Second Embodiment

2.1. Substance Detection Device

Figure 14:
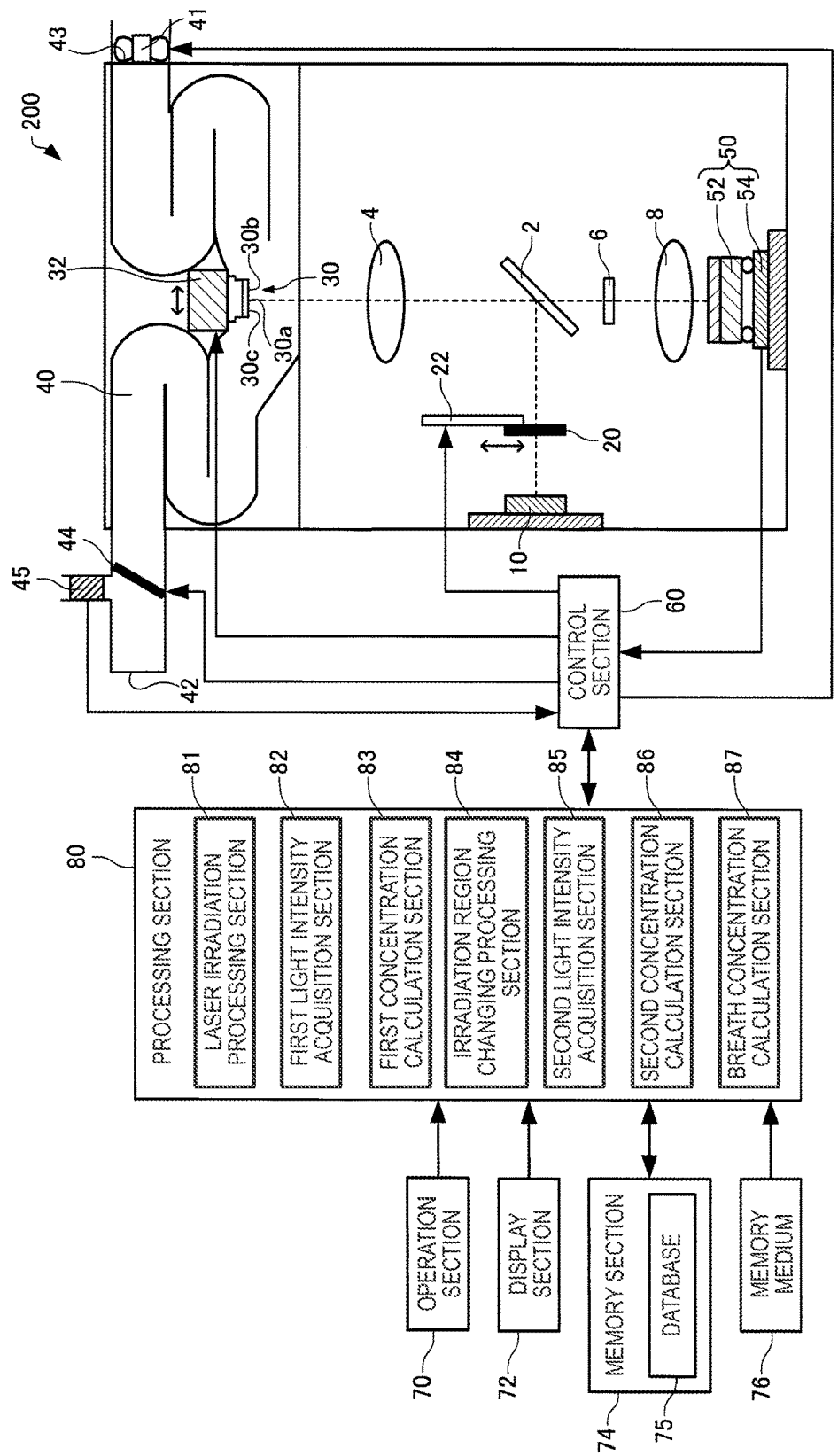
FIG. 14 is a view for explaining a substance detection device according to a second embodiment.

Next, a substance detection device according to a second embodiment will be described with reference to the drawings. FIG. 14 is a view for explaining a substance detection device 200 according to the second embodiment. Hereinafter, in the substance detection device 200, the same reference numerals are given to members having the same function as the constituent members of the above-mentioned substance detection device 100, and the detailed description thereof will be omitted.

As shown in FIG. 14, the substance detection device 200 is different from the above-mentioned substance detection device 100 in that the device includes a control valve 44 and a flow rate sensor 45. Further, the substance detection device 200 is different from the above-mentioned substance detection device 100 in that the processing section 80 also functions as a second light intensity acquisition section 85, a second concentration calculation section 86, and a breath concentration calculation section 87.

The control valve 44 is provided in the course of the flow path 40 from the suction port 42 to the sensor chip 30. The control valve 44 is provided, for example, in the vicinity of the suction port 42. The control valve 44 is, for example, opened and closed in response to a signal from the processing section 80. The sensor chip 30 is exposed to a given gas in a state where the control valve 44 is opened. Specifically, the sensor chip 30 is exposed to a first gas containing breath and air, and also exposed to the air in a state where the control valve 44 is opened. The air contains NO derived from, for example, an exhaust gas from cars or heaters. The control valve 44 may be opened and closed by hand.

The flow rate sensor 45 is provided in the flow path 40 in the vicinity of the control valve 44. The flow rate sensor 45 can detect the flow rate between the suction port 42 and the control valve 44 in the flow path 40. The form of the flow rate sensor 45 is not particularly limited as long as it can detect the flow rate.

The control section 60 controls the control valve 44 in response to a signal from the processing section 80.

Figure 15:
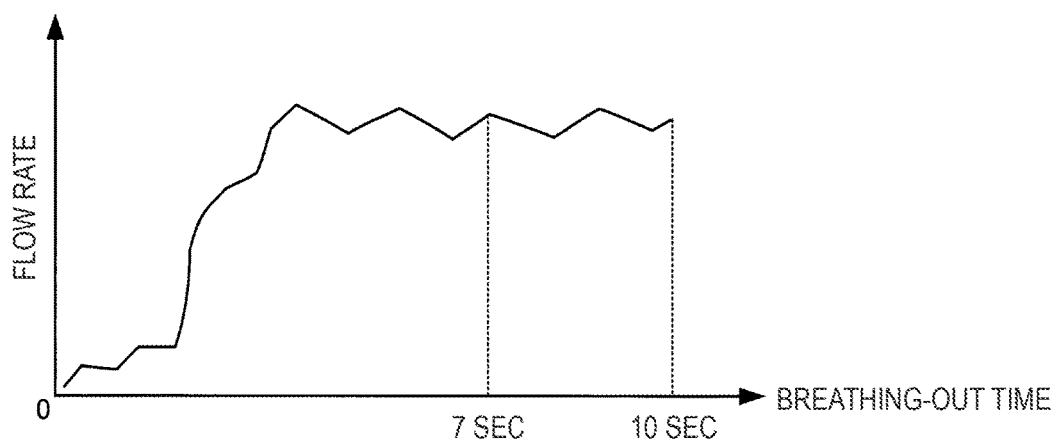
FIG. 15 is a graph showing a relationship between a breathing-out time and a flow rate.

For example, in the case where after a predetermined time (for example, 7 seconds) has elapsed from when the flow rate is detected by the flow rate sensor 45, and also for example, the flow rate detected by the flow rate sensor 45 at the time point when 7 seconds has elapsed is a predetermined value (for example, 50 mL/sec), the processing section 80 brings the control valve 44 in a closed state into an opened state only for a predetermined time (for example, 3 seconds). That is, for example, the processing section 80 brings the control valve 44 into an opened state only in a period between after 7 seconds to after 10 seconds from when the flow rate is detected by the flow rate sensor 45. For example, in the case where the concentration of NO in the breath is to be determined, as shown in FIG. 15, standardization is performed such that the breath in a "plateau phase" at a flow rate of 50 mL/sec in a period between after 7 seconds to after 10 seconds from when a user starts to breathe out is collected and measured.

The second light intensity acquisition section 85 performs second measurement processing by acquiring the intensity of Raman scattered light from a third region 30c of the sensor chip 30 exposed to the air detected by the light detector 50. The content of the processing of the second measurement processing is, for example, the same as the content of the processing of the first measurement processing described above. The third region 30c of the sensor chip 30 is a surface including an organic molecular modification film of the sensor chip 30 and is a different region from the regions 30a and 30b.

The second concentration calculation section 86 calculates the concentration of a target substance (NO) in the air based on the measurement result of the second measurement processing performed by the second light intensity acquisition section 85. Specifically, the second concentration calculation section 86 calculates the saturation intensity (predicted saturation intensity) of Raman scattered light by fitting from the measurement result of the second measurement processing in the same manner as the first concentration calculation section 83. Then, the second concentration calculation section 86 calculates the concentration of NO in the air.

The breath concentration calculation section 87 calculates the concentration of a target substance in the breath based on the intensity of Raman scattered light acquired by the first light intensity acquisition section 82 (the measurement result of the first measurement processing in the first concentration calculation section 83) and the intensity of Raman scattered light acquired by the second light intensity acquisition section 85 (the measurement result of the second measurement processing in the second concentration calculation section 86). In this embodiment, the first gas contains breath and air. Specifically, the breath concentration calculation section 87 calculates the concentration of NO in the breath from a difference between the concentration of NO in the first gas calculated by the first concentration calculation section 83 and the concentration of NO in the air calculated by the second concentration calculation section 86.

The substance detection device 200 includes the breath concentration calculation section 87 which calculates the concentration of a target substance in the breath based on the measurement result of the first measurement processing and the intensity of Raman scattered light acquired by the second light intensity acquisition section 85. Due to this, in the substance detection device 200, the concentration of NO in the breath can be accurately calculated from a difference between the concentration of NO in the first gas calculated by the first concentration calculation section 83 and the concentration of NO in the air calculated by the second concentration calculation section 86.

2.2. Substance Detection Method

Figure 16:
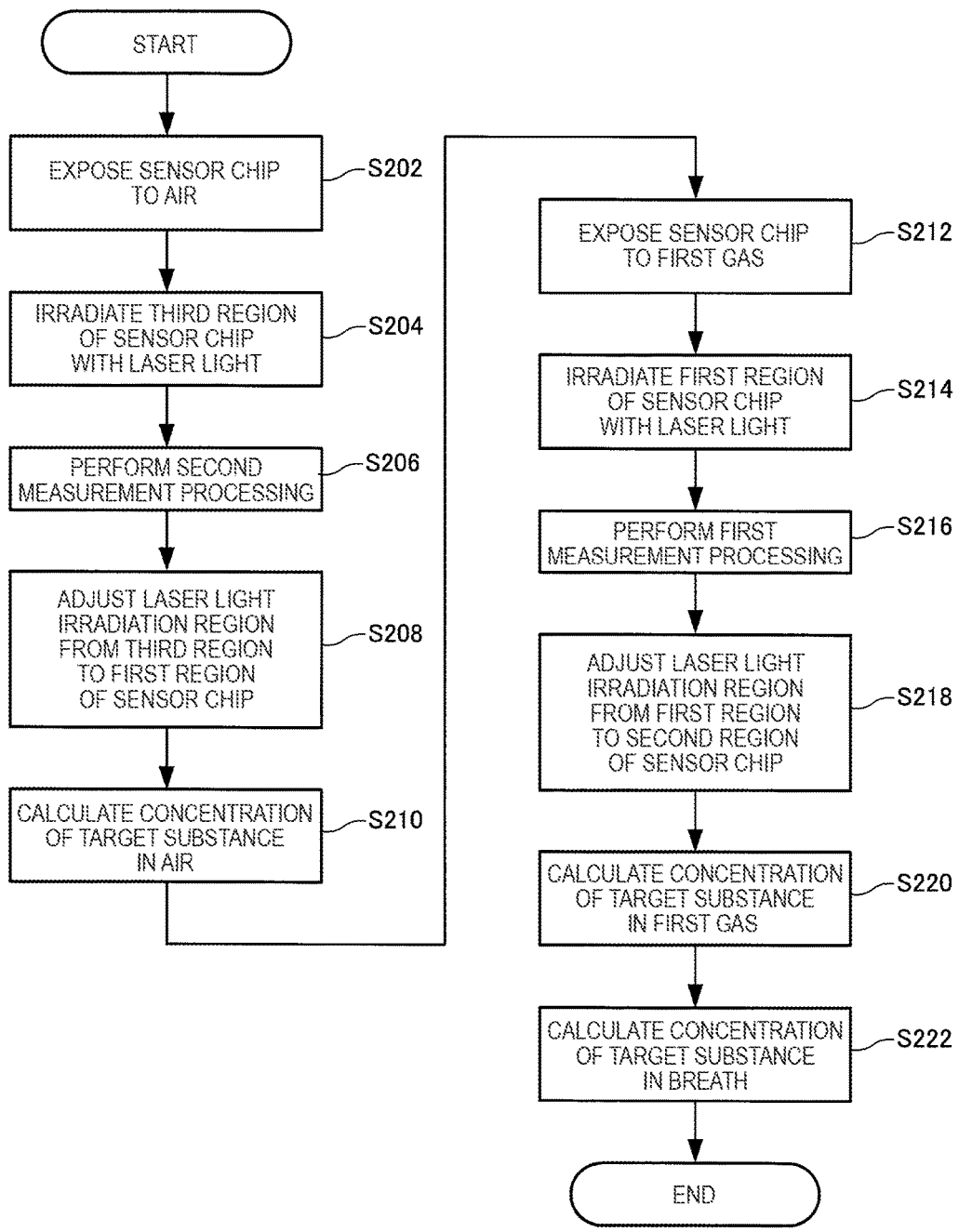
FIG. 16 is a flowchart for explaining a substance detection method according to a second embodiment.

Next, a substance detection method according to a second embodiment will be described with reference to the drawings. FIG. 16 is a flowchart for explaining the substance detection method according to the second embodiment. Hereinafter, a detection method using the substance detection device 200 will be described as the substance detection method according to the second embodiment. Hereinafter, with respect to the substance detection method according to the second embodiment, different points from the example of the substance detection method according to the first embodiment described above will be described, and the description of the same manner will be omitted or simply made.

First, the processing section 80 performs processing of exposing the sensor chip 30 to the air (S202). Specifically, the processing section 80 performs processing of opening the control valve 44 and also performs processing of driving the pump 41 in response to an operation signal from the operation section 70. By doing this, the air flows in the flow path 40, and therefore, the sensor chip 30 can be exposed to the air. The flow rate of the air in the flow path 40 is, for example, 1 mL/sec or more and 100 mL/sec or less, preferably 50 mL/sec.

Subsequently, the laser irradiation processing section 81 performs processing of irradiating the third region 30c of the sensor chip 30 exposed to the air with laser light (S204). Specifically, the laser irradiation processing section 81 removes the light-blocking filter 20 from the optical axis of the laser light by controlling the light-blocking filter moving section 22 after a predetermined time (for example, after 5 seconds to 30 seconds) has elapsed from when the pump 41 is driven. By doing this, the third region 30c is irradiated with the laser light.

Subsequently, the second light intensity acquisition section 85 performs second measurement processing by acquiring the intensity of Raman scattered light from the third region 30c of the sensor chip 30 detected by the light detector 50 (S206). Specifically, the second light intensity acquisition section 85 acquires the intensity of Raman scattered light a plurality of times at predetermined intervals based on the timing of irradiation of the third region 30c. For example, the laser irradiation processing section 81 outputs a signal to the second light intensity acquisition section 85 at the same time that the laser irradiation processing section 81 completes the processing of removing the light-blocking filter 20 from the optical axis of the laser light by controlling the light-blocking filter moving section 22. The second light intensity acquisition section 85 starts the second measurement processing in response to the signal from the laser irradiation processing section 81.

Subsequently, the irradiation region changing processing section 84 performs processing of moving the light-blocking filter 20 to the optical axis of the laser light and blocking the laser light by controlling the light-blocking filter moving section 22 after the second measurement processing (for example, in response to a signal of completion of the second measurement from the second light intensity acquisition section 85). After blocking the laser light, the irradiation region changing processing section 84 performs processing of moving the sensor chip 30 and adjusting the laser light irradiation region from the third region 30c to the first region 30a of the sensor chip 30 by controlling the irradiation region changing section 32 (S208).

Subsequently, the second concentration calculation section 86 calculates the concentration of the target substance (NO) in the air based on the measurement result of the second measurement processing performed by the second light intensity acquisition section 85 (S210). Incidentally, the processing of calculating the concentration of NO in the air (S210) may be performed after the second measurement processing (S206) and before the processing of adjusting the laser light irradiation region from the third region 30c to the first region 30a (S208).

Subsequently, the sensor chip 30 is exposed to a first gas containing breath and air (S212). Specifically, the processing section 80 performs processing of closing the control valve in response to an operation signal from the operation section 70 operated by a user. Subsequently, the user breathes into the device from the suction port 42 through, for example, a mouth piece. The processing section 80, for examples, brings the control valve 44 into an opened state only in a period between after 7 seconds to after 10 seconds from when the flow rate is detected by the flow rate sensor 45. By doing this, the sensor chip 30 can be exposed to the first gas containing breath and air.

Subsequently, the laser irradiation processing section 81 performs processing of irradiating the first region 30a of the sensor chip 30 exposed to the first gas with laser light (S214). Specifically, the laser irradiation processing section 81 removes the light-blocking filter 20 from the optical axis of the laser light by controlling the light-blocking filter moving section 22 after a predetermined time (for example, after 5 seconds to 30 seconds) has elapsed from when the processing of closing the control valve 44 is performed after the sensor chip 30 is exposed to the first gas. By doing this, the first region 30a is irradiated with the laser light.

The processing (S216) to the processing (S220) to be performed subsequently are the same as the processing (S106) to the processing (S110), respectively, described in the above-mentioned "1.2. Substance DetectionMethod". Therefore, the description thereof will be omitted.

Subsequently, the breath concentration calculation section 87 calculates the concentration of a target substance in the breath based on the intensity of Raman scattered light acquired by the first light intensity acquisition section 82 (the measurement result of the first measurement processing in the first concentration calculation section 83) and the intensity of Raman scattered light acquired by the second light intensity acquisition section 85 (the measurement result of the second measurement processing in the second concentration calculation section 86) (S222). Specifically, the breath concentration calculation section 87 calculates the concentration of NO in the breath from a difference between the concentration of NO in the first gas calculated by the first concentration calculation section 83 and the concentration of NO in the air calculated by the second concentration calculation section 86. Then, the processing section 80 outputs a signal for displaying the concentration of NO in the breath in the display section 72, and the processing is completed.

In the substance detection method according to the second embodiment, the concentration of NO in the breath can be accurately calculated as described in "2.1. Substance Detection Device".

3. Third Embodiment

3.1. Substance Detection Device

Figure 17:
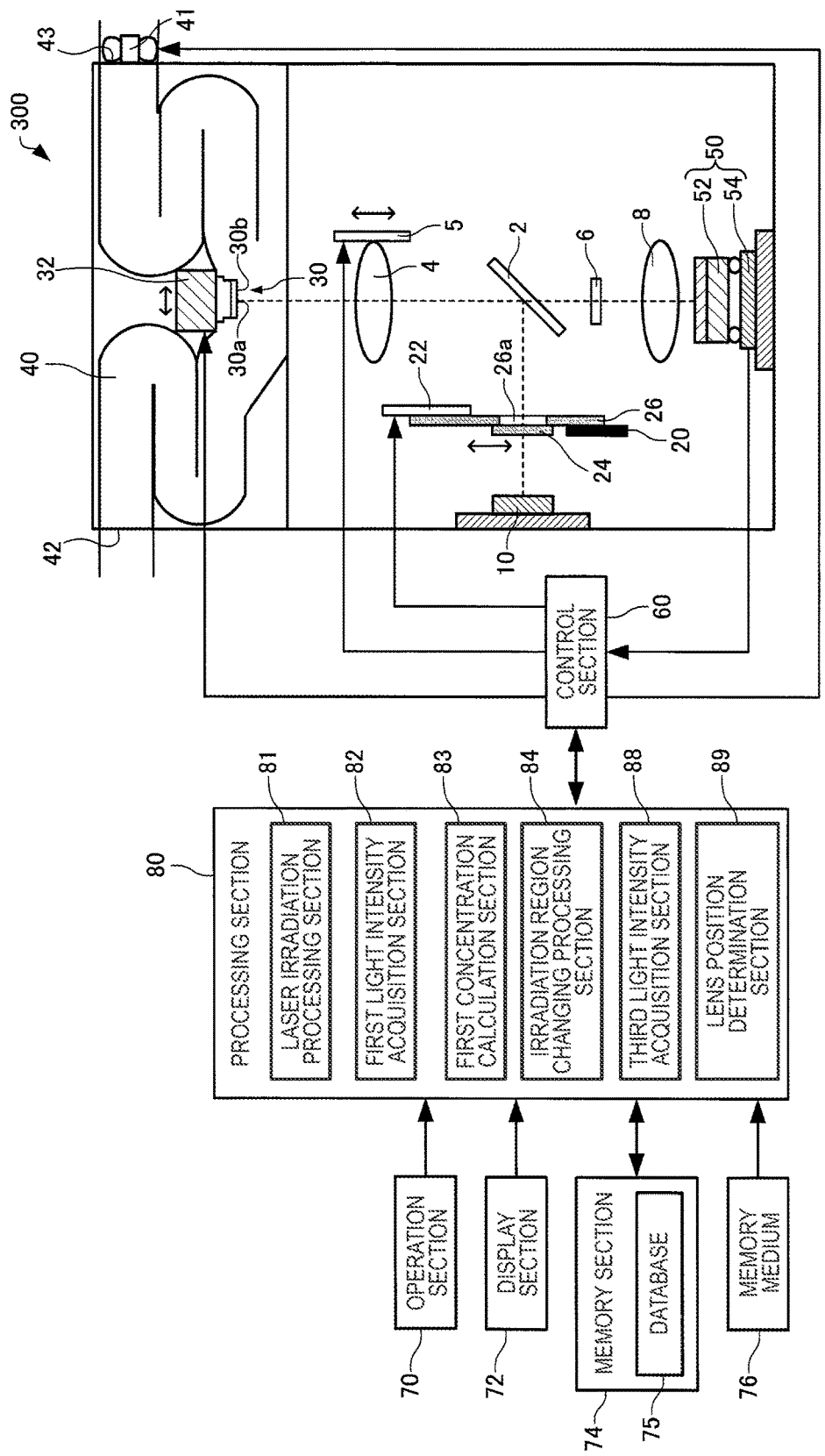
FIG. 17 is a view for explaining a substance detection device according to a third embodiment.

Next, a substance detection device according to a third embodiment will be described with reference to the drawings. FIG. 17 is a view for explaining a substance detection device 300 according to the third embodiment. Hereinafter, in the substance detection device 300, the same reference numerals are given to members having the same function as the constituent members of the above-mentioned substance detection device 100, and the detailed description thereof will be omitted.

As shown in FIG. 17, the substance detection device 300 is different from the above-mentioned substance detection device 100 in that the device includes a first dimmer filter 24, a second dimmer filter 26, and a lens moving section 5. Further, the substance detection device 300 is different from the above-mentioned substance detection device 100 in that the processing section 80 also functions as a third light intensity acquisition section 88 and a lens position determination section 89.

The first dimmer filter 24 and the second dimmer filter 26 can decrease the intensity of laser light emitted from the light source 10. The first dimmer filter 24 is set such that the intensity of the laser light transmitted through the first dimmer filter 24 is, for example, 0.01 mW or more and 0.1 mW or less, preferably 0.05 mW. The second dimmer filter 26 is set such that the intensity of the laser light transmitted through the second dimmer filter 26 is higher than the intensity of the laser light transmitted through the first dimmer filter 24. The intensity of the laser light transmitted through the second dimmer filter 26 is, for example, 0.1 mW or more and 2 mW or less, preferably 0.1 mW or more and 0.5 mW or less, more preferably 0.5 mW. The laser light transmitted through the first dimmer filter 24 is irradiated on the sensor chip 30 as second laser light.

Incidentally, for example, in the case where the intensity of laser light emitted from the light source 10 (the intensity of laser light which is not transmitted through the dimmer filters 24 and 26) is 0.1 mW or more and 2 mW or less, the second dimmer filter 26 may not be provided.

The shape of the first dimmer filter 24 and the second dimmer filter 26 may be a plate or a film. The material of the dimmer filters 24 and 26 is not particularly limited as long as it can decrease the intensity of the laser light emitted from the light source 10. In the example shown in the drawing, an opening 26a is provided in the second dimmer filter 26, and the laser light transmitted through the first dimmer filter 24 passes through the opening 26a.

The first dimmer filter 24 and the second dimmer filter 26 are supported by the light-blocking filter moving section 22. The light-blocking filter moving section 22 moves the dimmer filters 24 and 26. That is, the light-blocking filter moving section 22 functions as a first dimmer filter moving section which moves the first dimmer filter 24 and also functions as a second dimmer filter moving section which moves the second dimmer filter 26. Although not shown in the drawing, the substance detection device 300 may include a first dimmer filter moving section which moves the first dimmer filter 24 and may also include a second dimmer filter moving section which moves the second dimmer filter 26 separately from the light-blocking filter moving section 22.

The lens moving section 5 moves the lens 4. In the example shown in the drawing, the lens moving section 5 moves the lens 4 in a direction parallel to the optical axis of the laser light directed from the half mirror 2 to the sensor chip 30. The lens moving section 5 includes, for example, a support section which supports the lens 4 and a driving section which moves the support section, and can move the lens 4 by driving the driving section in response to a signal from the processing section 80 thereby moving the support section. The driving section of the lens moving section 5 is, for example, a motor. The lens 4 guides the laser light to the sensor chip 30.

The control section 60 moves the lens 4 by controlling the lens moving section 5 in response to a signal from the processing section 80.

The third light intensity acquisition section 88 acquires the intensity of scattered light from the first region 30a by the laser light transmitted through the first dimmer filter 24 detected by the light detector 50 in a state where the lens 4 is moved by the lens moving section 5. The third light intensity acquisition section 88 may acquire the intensity of Raman scattered light derived from the organic molecular modification film 134 from the first region 30a or may acquire the intensity of light (fluorescence) emitted from the background derived from aniline in the case where the modifying molecule of the organic molecular modification film 134 is aniline.

The lens position determination section 89 determines the position of the lens 4 based on the intensity of scattered light acquired by the third light intensity acquisition section 88. Specifically, the lens position determination section 89 moves the lens 4 and determines the position of the lens 4 by controlling the lens moving section 5 so that the light intensity acquired by the third light intensity acquisition section 88 becomes the maximum in response to a signal from the third light intensity acquisition section 88. For example, when the light intensity acquired by the third light intensity acquisition section 88 is increased in the case where the lens 4 is moved in a direction away from the sensor chip 30, the lens position determination section 89 performs processing of moving the lens 4 in a direction further away from the sensor chip 30. Then, when the light intensity acquired by the third light intensity acquisition section 88 is decreased, the lens position determination section 89 performs processing of bringing the lens 4 closer to the sensor chip 30 to the contrary. In this manner, the lens position determination section 89 performs feedback detection of the light intensity acquired by the third light intensity acquisition section 88 so that the light intensity acquired by the third light intensity acquisition section 88 becomes the maximum.

The substance detection device 300 includes the third light intensity acquisition section 88 which acquires the intensity of scattered light from the first region 30a by the second laser light transmitted through the first dimmer filter 24 in a state where the lens 4 is moved by the lens moving section 5 and the lens position determination section 89 which determines the position of the lens 4 based on the intensity of scattered light acquired by the third light intensity acquisition section 88. In this manner, in the substance detection device 300, the position of the lens 4 can be determined by using the second laser light with a lower intensity than the first laser light irradiated on the first region 30a for performing the first measurement processing. Due to this, in the substance detection device 300, defocus caused by, for example, moving the sensor chip 30 can be corrected while reducing the deterioration of the sensor chip 30 by irradiation with the laser light as compared with the case where the position of the lens 4 is determined by using the first laser light.

3.2. Substance Detection Method

Figure 18:
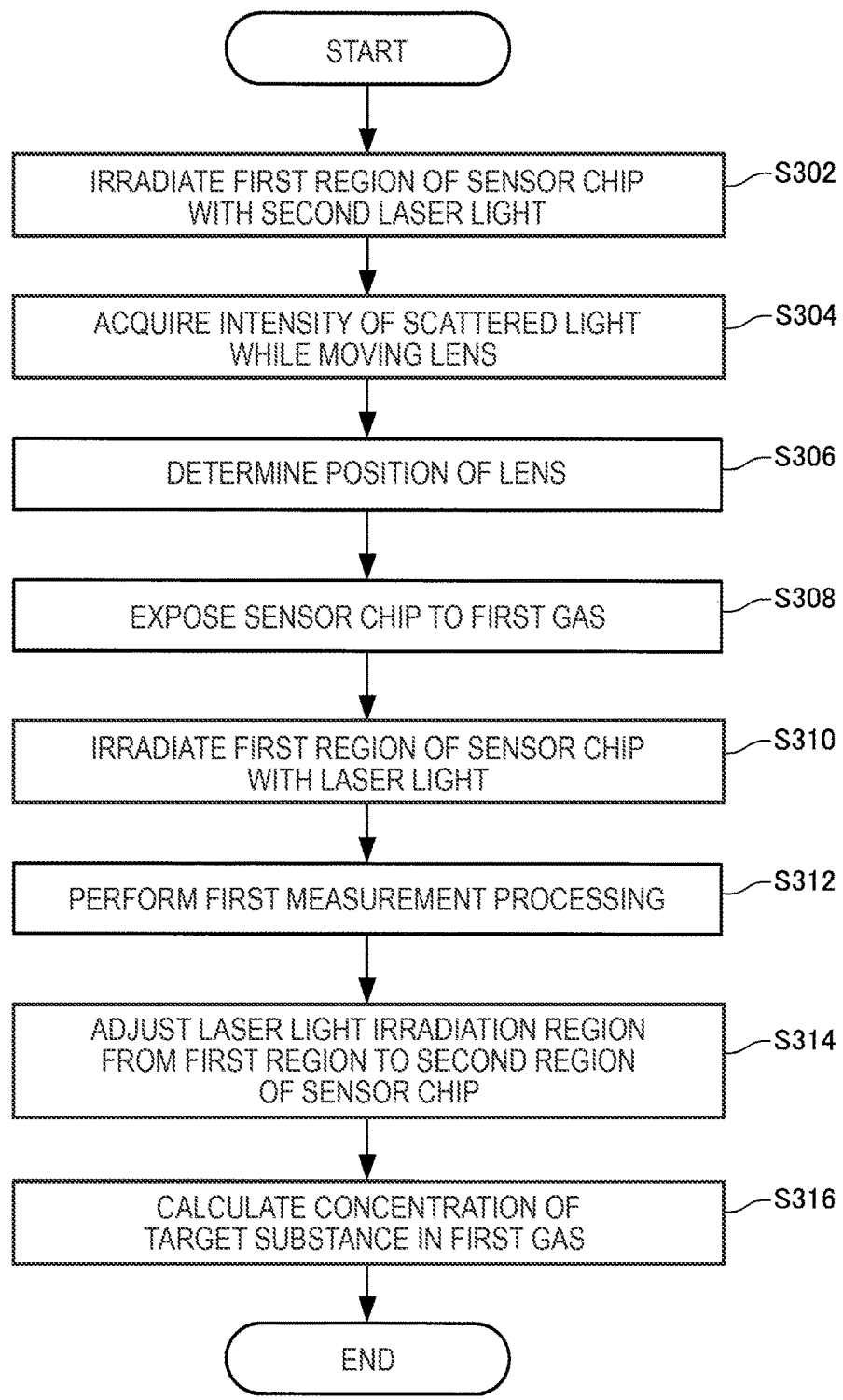
FIG. 18 is a flowchart for explaining a substance detection method according to a third embodiment.

Next, a substance detection method according to a third embodiment will be described with reference to the drawings. FIG. 18 is a flowchart for explaining the substance detection method according to the third embodiment. Hereinafter, a detection method using the substance detection device 300 will be described as the substance detection method according to the third embodiment. Hereinafter, with respect to the substance detection method according to the third embodiment, different points from the example of the substance detection method according to the first embodiment described above will be described, and the description of the same manner will be omitted or simply made.

First, the laser irradiation processing section 81 performs processing of irradiating the first region 30a of the sensor chip 30 with second laser light (S302). Specifically, the laser irradiation processing section 81 removes the light-blocking filter 20 from the optical axis of the laser light and disposes the first dimmer filter 24 on the optical axis of the laser light by controlling the light-blocking filter moving section 22 in response to an operation signal from the operation section 70. By doing this, the first region 30a can be irradiated with the second laser light with a lower intensity than the first laser light through the lens 4. The first laser light is laser light which is emitted from the light source 10 and is not transmitted through the first dimmer filter 24.

Subsequently, the third light intensity acquisition section 88 acquires the intensity of scattered light from the first region 30a of the sensor chip 30 by the second laser light detected by the light detector 50 in a state where the lens 4 is moved by the lens moving section 5 (S304).

Subsequently, the lens position determination section 89 determines the position of the lens 4 based on the intensity of scattered light from the first region 30a acquired by the third light intensity acquisition section 88 (S306). Specifically, the lens position determination section 89 moves the lens 4 and determines the position of the lens 4 by controlling the lens moving section 5 so that the light intensity acquired by the third light intensity acquisition section 88 becomes the maximum in response to a signal from the third light intensity acquisition section 88.

Subsequently, the processing section 80 performs processing of exposing the sensor chip 30 to a first gas (for example, an NO gas) (S308). Specifically, the processing section 80 performs processing of driving the pump 41 in response to a signal from the lens position determination section 89. By doing this, the NO gas flows in the flow path 40, and therefore, the sensor chip 30 can be exposed to the NO gas. The processing of exposure to the first gas (S308) may be performed before the processing of irradiation with the second laser light (S302).

Subsequently, the laser irradiation processing section 81 performs processing of irradiating the first region 30a of the sensor chip 30 exposed to the NO gas with laser light (first laser light) (S310). Specifically, the laser irradiation processing section 81 removes the first dimmer filter 24 from the optical axis of the laser light and disposes the second dimmer filter 26 on the optical axis of the laser light by controlling the light-blocking filter moving section 22 after a predetermined time (for example, after 30 seconds) has elapsed from when the pump 41 is driven. By doing this, the first region 30a is irradiated with the first laser light with a higher intensity than the second laser light. The first region 30a is irradiated with the first laser light through the lens 4.

The processing (S312) to the processing (S316) to be performed subsequently are the same as the processing (S106) to the processing (S110), respectively, described in the above-mentioned "1.2. Substance Detection Method". Therefore, the description thereof will be omitted.

In the substance detection method according to the third embodiment, defocus caused by, for example, moving the sensor chip 30 can be corrected while reducing the deterioration of the sensor chip 30 by irradiation with the laser light as described in "3.1. Substance Detection Device".

4. Fourth Embodiment

4.1. Substance Detection Device

Figure 19:
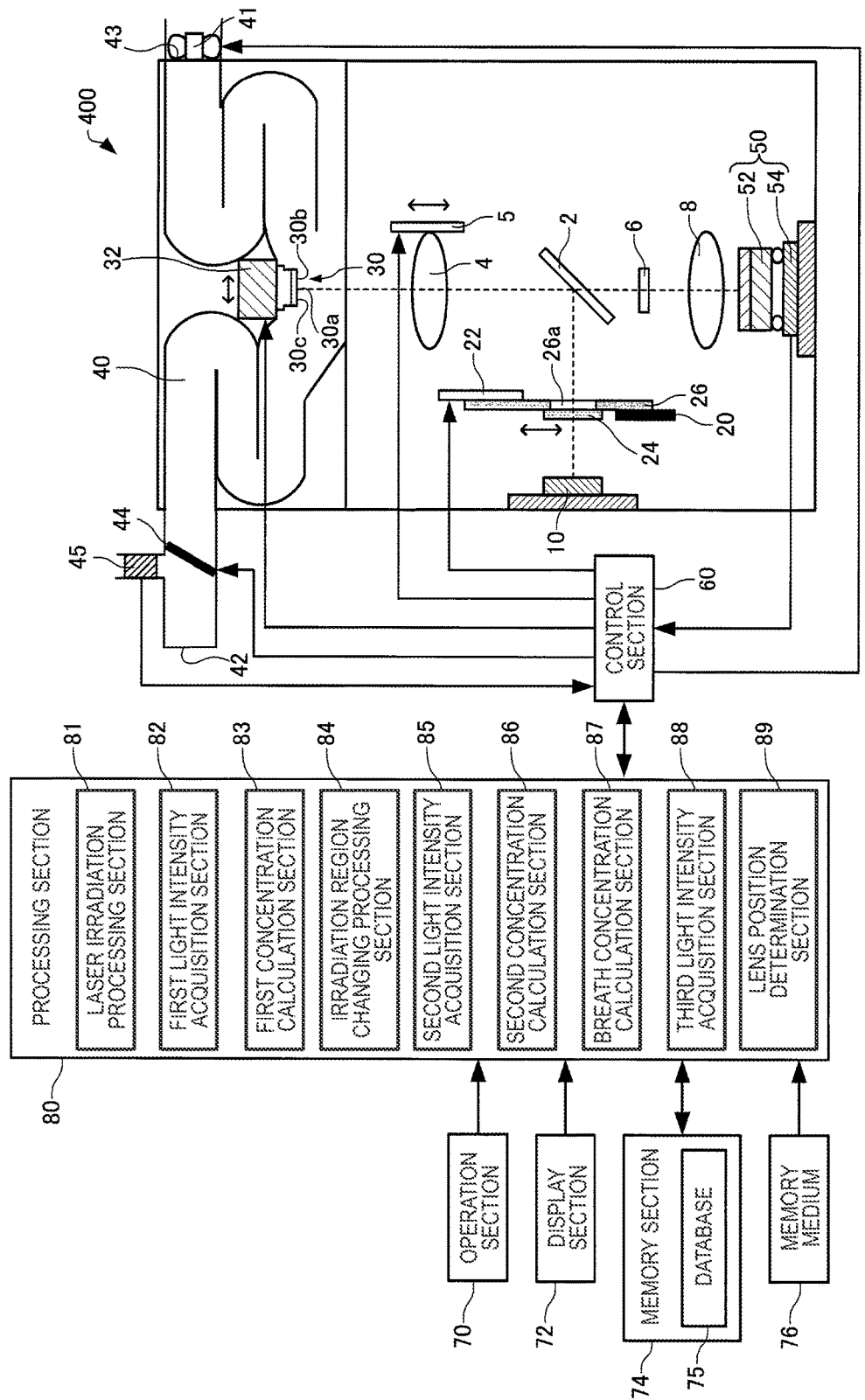
FIG. 19 is a view for explaining a substance detection device according to a fourth embodiment.

Next, a substance detection device according to a fourth embodiment will be described with reference to the drawings. FIG. 19 is a view for explaining a substance detection device 400 according to the fourth embodiment. Hereinafter, in the substance detection device 400, the same reference numerals are given to members having the same function as the constituent members of the above-mentioned substance detection devices 100, 200, and 300, and the detailed description thereof will be omitted.

As shown in FIG. 19, the substance detection device 400 is different from the above-mentioned substance detection device 100 in that the device includes a control valve 44, a flow rate sensor 45, a first dimmer filter 24, a second dimmer filter 26, and a lens moving section 5. Further, the substance detection device 400 is different from the above-mentioned substance detection device 100 in that the processing section 80 also functions as a second light intensity acquisition section 85, a second concentration calculation section 86, a breath concentration calculation section 87, a third light intensity acquisition section 88, and a lens position determination section 89. In this embodiment, the first gas contains breath and air.

In the substance detection device 400, the concentration of NO in the breath can be accurately calculated from a difference between the concentration of NO in the first gas calculated by the first concentration calculation section 83 and the concentration of NO in the air calculated by the second concentration calculation section 86 in the same manner as in the substance detection device 200. Further, in the substance detection device 400, defocus caused by, for example, moving the sensor chip 30 can be corrected while reducing the deterioration of the sensor chip 30 by irradiation with the laser light in the same manner as in the substance detection device 300.

4.2. Substance Detection Method

Figure 20:
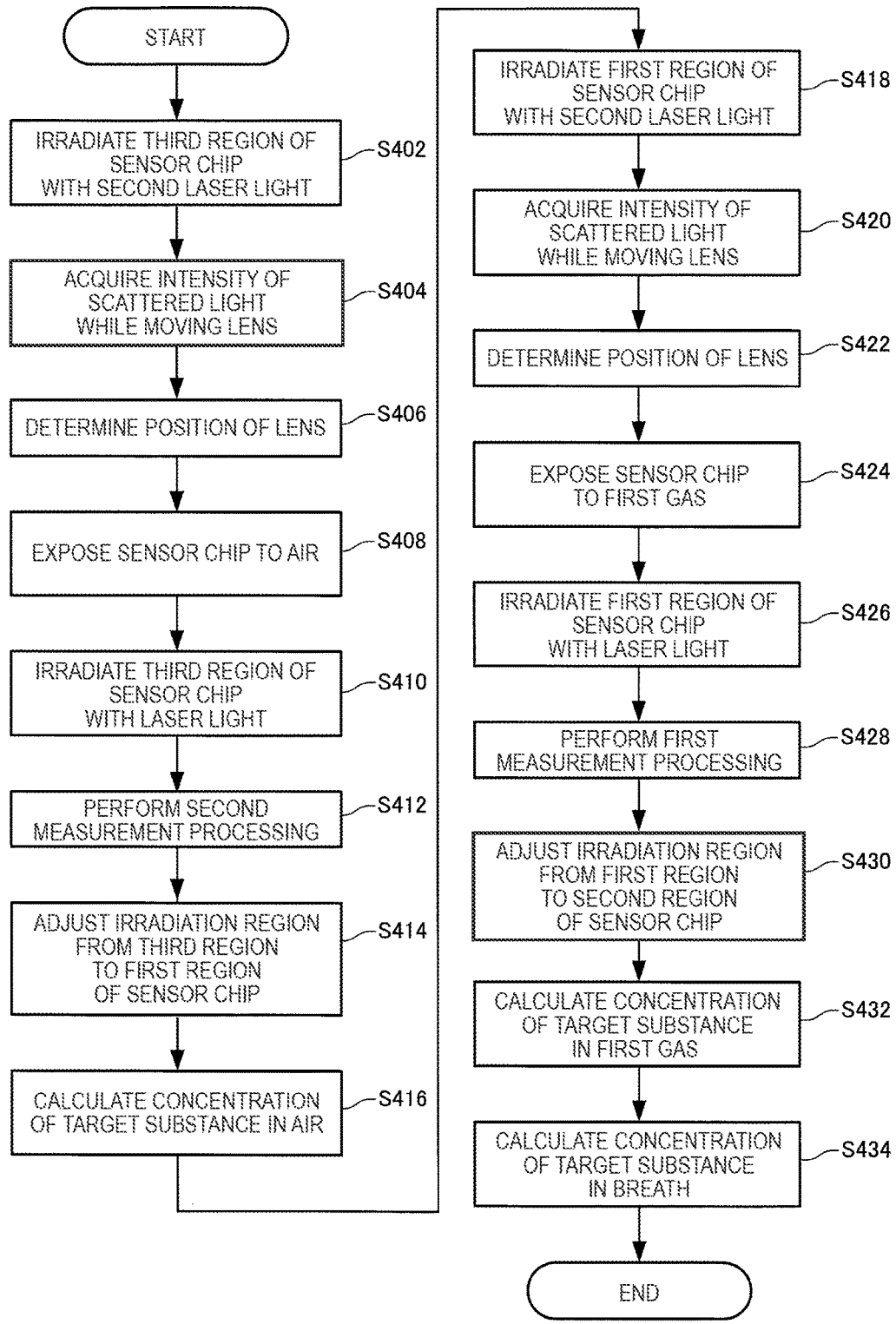
FIG. 20 is a flowchart for explaining a substance detection method according to a fourth embodiment.

Next, a substance detection method according to a fourth embodiment will be described with reference to the drawings. FIG. 20 is a flowchart for explaining the substance detection method according to the fourth embodiment. Hereinafter, a detection method using the substance detection device 400 will be described as the substance detection method according to the fourth embodiment. Hereinafter, with respect to the substance detection method according to the fourth embodiment, different points from the examples of the substance detection methods according to the first, second, and third embodiments described above will be described, and the description of the same manner will be omitted or simply made.

First, the laser irradiation processing section 81 performs processing of irradiating the third region 30c of the sensor chip 30 with second laser light (S402).

Subsequently, the third light intensity acquisition section 88 acquires the intensity of scattered light from the third region 30c of the sensor chip 30 by the second laser light in a state where the lens 4 is moved by the lens moving section 5 (S404).

Subsequently, the lens position determination section 89 determines the position of the lens 4 based on the intensity of scattered light acquired by the third light intensity acquisition section 88 (S406).

Subsequently, the processing section 80 performs processing of exposing the sensor chip 30 to the air (S408). Specifically, the processing section 80 performs processing of opening the control valve 44 and also performs processing of driving the pump 41 in response to a signal from the lens position determination section 89.

Subsequently, the laser irradiation processing section 81 performs processing of irradiating the third region 30c of the sensor chip 30 exposed to the air with laser light (first laser light) (S410).

The processing (S412) to the processing (S416) to be performed subsequently are the same as the processing (S206) to the processing (S210), respectively, described in the above-mentioned "2.2. Substance Detection Method". Therefore, the description thereof will be omitted.

Subsequently, the laser irradiation processing section 81 performs processing of irradiating the first region 30a of the sensor chip 30 with second laser light (S418). Specifically, the laser irradiation processing section 81 removes the second dimmer filter 26 from the optical axis of the laser light and disposes the first dimmer filter 24 on the optical axis of the laser light by controlling the light-blocking filter moving section 22 after the concentration of the target substance in the air is calculated.

The processing (S420) to the processing (S432) to be performed subsequently are the same as the processing (S304) to the processing (S316), respectively, described in the above-mentioned "3.2. Substance Detection Method". Therefore, the description thereof will be omitted.

The processing (S434) to be performed subsequently is the same as the processing (S222) described in the above-mentioned "2.2. Substance Detection Method". Therefore, the description thereof will be omitted.

In the substance detection method according to the fourth embodiment, the concentration of NO in the breath can be accurately calculated, and also defocus caused by, for example, moving the sensor chip 30 can be corrected while reducing the deterioration of the sensor chip 30 by irradiation with the laser light as described in "4.1. Substance Detection Device".

The above-mentioned embodiments and modification examples are merely examples, and the invention is not limited thereto. For example, the respective embodiments and modification examples can be appropriately combined.

The substance detection device and the substance detection method according to the invention can be widely applied to a target substance which can be detected by SERS using an organic molecular modification film containing a modifying molecule derived from a compound having an amine-based or sulfur-based functional group other than NO. Specific examples of the target substance include VOC gases such as toluene. In addition, the invention can also be applied to surface-enhanced infrared absorption spectroscopy (SEIRAS) using surface plasmon resonance other than the SERS method.

The invention includes substantially the same configurations (for example, configurations having the same function, method, and result, or configurations having the same object and effect) as the configuration described in the embodiment. Further, the invention includes configurations in which a nonessential part of the configuration described in the embodiment is replaced. In addition, the invention includes configurations having the same operational effect as that of the configuration described in the embodiment, or configurations capable of achieving the same object. Moreover, the invention includes configurations in which a known art is added to the configuration described in the embodiment.

The entire disclosure of Japanese Patent Application No. 2015-175684, filed Sep. 7, 2015 is expressly incorporated by reference herein.

What is claimed is:

1. A nitric oxide (NO) detection method, comprising:
    exposing a sensor chip for surface-enhanced Raman scattering having a metal microstructure and an organic molecular modification film comprising ammonia, aniline, DAR-4M, or dimethyl sulfide, which modifies the metal microstructure to a first gas comprising the NO;
    irradiating a first region of the sensor chip exposed to the first gas with first laser light;
    performing a first measurement by detecting Raman scattered light from the first region of the sensor chip and acquiring the intensity of the Raman scattered light;
    blocking the first laser light after the performing the first measurement;
    calculating the concentration of NO in the first gas by comparing the acquired intensity of the Raman scattered light to a stored NO calibration curve; and
    adjusting an irradiation region where the sensor chip is irradiated with the first laser light from the first region to a second region which is different from the first region of the sensor chip after the blocking the first laser light.

2. The NO detection method according to claim 1, wherein in the adjusting the first laser light irradiation region to the second region, the sensor chip is moved.

3. The NO detection method according to claim 1, wherein in the performing the first measurement, the intensity of Raman scattered light is acquired a plurality of times at predetermined intervals based on the timing of irradiation of the first region in order to determine a saturation intensity.

4. The NO detection method according to claim 1, wherein
    the first gas further comprises breath, and
    the method further includes:
        exposing the sensor chip to air;
        irradiating a third region of the sensor chip exposed to the air, which is different from the first region and the second region of the sensor chip exposed to the first gas, with the first laser light;
        acquiring a second intensity of Raman scattered light from the third region;
        calculating the concentration of NO in the air by comparing the second acquired intensity of the Raman scattered light to a stored NO calibration curve; and
        calculating the concentration of NO in the breath based on a difference between the concentration of NO in the first gas and the concentration of NO in the air.

5. The NO detection method according to claim 1, wherein the method further includes:
    irradiating the first region with second laser light with a lower intensity than the first laser light through a lens before the irradiating the first laser light,
    acquiring the intensity of scattered light from the first region by the second laser light detected in a state where the lens is moved, and
    determining the position of the lens to provide a maximum intensity for the second laser based on the acquired intensity of the scattered light from the first region, and
    in the irradiating the first laser light, the first region is irradiated through the lens.

6. The NO detection method according to claim 1, wherein
    the first gas contains nitrogen monoxide.

* * * * *